| United States Patent [19] | [11] Patent Number: 4,623,650 |
| Gilligan et al. | [45] Date of Patent: Nov. 18, 1986 |

[54] ANTIBIOTIC DERIVATIVES OF 7-PHENYL-1,4-DIHYDRO-4-OXO-3-QUINOLINECARBOXYLIC ACIDS

[75] Inventors: Paul J. Gilligan, New Haven; Paul R. McGuirk, Gales Ferry, both of Conn.; Michael J. Witty, Dover, Great Britain

[73] Assignee: Pfizer Inc., New York, N.Y.

[21] Appl. No.: 679,150

[22] Filed: Dec. 6, 1984

[51] Int. Cl.[4] .................. A61K 31/47; A61K 31/537; C07D 215/18
[52] U.S. Cl. .................................... 514/312; 514/236; 546/156; 544/101
[58] Field of Search ............. 546/156; 424/258; 544/101; 514/236

[56] References Cited

U.S. PATENT DOCUMENTS

| 3,472,859 | 10/1969 | Lesher | 260/287 |
| 3,907,808 | 9/1975 | Lesher | 546/156 |
| 4,398,029 | 8/1983 | Irikura | 546/156 |
| 4,443,447 | 4/1984 | Gerster | 544/344 |

OTHER PUBLICATIONS

Koga J. Medicinal Chemistry 23, 1358–1363 (1980).

*Primary Examiner*—Sidney Marantz
*Assistant Examiner*—Robert Benson
*Attorney, Agent, or Firm*—Charles J. Knuth; Peter C. Richardson; Gezina Holtrust

[57] ABSTRACT

1-Substituted-6-fluoro-7-aryl-(8-fluoro)-1,4-dihydroquinol-4-one 3-carboxylic acids having antibacterial activity are prepared by reacting the corresponding alkyl 1-substituted-6-fluoro-7-bromo-(8-fluoro)-1,4-dihydroquinol-4-one-3-carboxylate with an arylmetallic compound and hydrolyzing the ester formed.

17 Claims, No Drawings

ANTIBIOTIC DERIVATIVES OF 7-PHENYL-1,4-DIHYDRO-4-OXO-3-QUINOLINECARBOXYLIC ACIDS

Background of the Invention

This invention relates to 1-substituted-6-fluoro7-aryl-(8-fluoro)-1,4-dihydro-quinol-4-one 3-carboxylic acids and their esters and cation salts, their preparation, antibacterial compositions containing these compounds and a method of using these compounds.

Since the introduction of nalidixic acids in 1963, a considerable number of patents and scientific papers have been published on analogs of this compound. Representative of these publications is U.S. Pat. No. 3,472,859 granted Oct. 14, 1969 disclosing inter alia compounds of the following formula

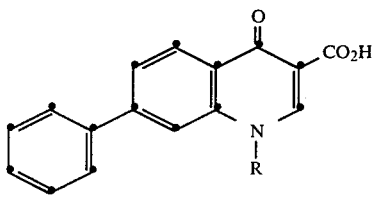

wherein R is lower alkyl. Example 7 of the patent discloses fungistatic activity for the compound wherein R is methyl, but no antibacterial data are provided.

SUMMARY OF THE INVENTION

The compounds of the present invention are 1,4-dihydroquinol-4-one-3-carboxylic acids for the formula

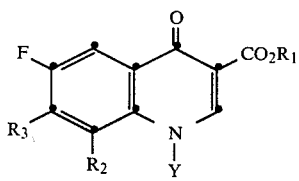

I wherein
$R_1$ is hydrogen, alkyl of 1 to 6 carbon atoms, benzyl or a pharmaceutically acceptable cation;
$R_2$ is hydrogen or fluoro;
Y is selected from the group consisting of alkyl, haloalkyl and polyhaloalkyl of 1 to 3 carbon atoms, hydroxyethyl, cyclopropyl, vinyl, allyl, phenyl, 4-hydroxyphenyl and 4-fluorophenyl;
$R_2$ and Y when taken together have the formula

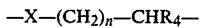

wherein
X is $CH_2$, O, S, NH, or $NCH_3$,
n is 0, 1 or 2, and
$R_4$ is selected from the group consisting of hydrogen, alkyl and haloalkyl of 1 to 3 carbons, hydroxymethyl, hydroxyethyl, aminomethyl, phenyl and methylene; and
$R_3$ is phenyl which may be substituted by one to three substituents selected from the group consisting of alkyl of 1 to 4 carbon atoms, alkoxy of 1 to 4 carbon atoms, alkylmercapto of 1 to 4 carbon atoms, alkylsulfinyl of 1 to 4 carbon atoms, alkylsulfonyl of 1 to 4 carbon atoms, halogen, trihalomethyl, hydroxy, hydroxyalkyl of 1 to 3 carbon atoms, methoxy, amino, alkylamino of 1 to 4 carbon atoms, dialkylamino of 2 to 8 carbon atoms, aminoalkyl of 1 to 3 carbon atoms, alkylaminoalkyl of 2 to 8 carbon atoms, dialkylaminoalkyl of 3 to 9 carbon atoms, formamido, alkanoylamino of 2 or 3 carbon atoms, formamidino, aminosulfonyl, alkylaminosulfonyl of 1 to 4 carbon atoms, dialkylaminosulfonyl of 2 to 8 carbon atoms, nitro, formyl, alkanoyloxy of 1 to 4 carbon atoms, ureido, alkylsulfonylamido of 1 to 4 carbon atoms, cyano, carboxamido, azidomethyl and carboxy;

with the proviso that $R_4$ is not methyl, when $R_3$ is phenyl or phenyl substituted by one or two substituents selected from alkyl, alkoxy, halogen, hydroxy, amino, alkylamino, alkanoylamino and formamido, and Z is $CH_2$, O or $NCH_3$.

Preferred compounds of the invention are those wherein $R_3$ is phenyl which may be monosubstituted at the 2, 3 or 4 position by a substituent selected from the group consisting of hydroxy, hydroxymethyl, methoxy, amino, methylamino, aminomethyl, carboxy, formamido, nitro, aminosulfonyl, methylsulfinyl, methylsulfonyl, acetylamido, N-(N',N'-dimethylformamidino), cyano and formyl. $R_3$ may in addition be substituted in any one of the unsubstituted positions by a substituent selected from the group consisting of fluoro, chloro, methyl, hydroxymethyl, aminomethyl, hydroxy, methoxy, methylthio, methylsulfinyl, methylsulfonyl, amino, methylamino, dimethylamino, nitro, carboxamido, aminosulfonyl, cyano and formyl.

Other preferred compounds are those wherein $R_1$ is hydrogen, or a pharmaceutically acceptable cation, and those wherein Y is ethyl in view of greater pharmaceutical activity.

Specific preferred compounds of the invention in which $R_2$ is fluorine are
6,8-difluoro-7-phenyl-1-ethyl-1,4-dihydroquinol-4-one 3-carboxylic acid
6,8-difluoro-7-(4-hydroxyphenyl)-1-ethyl-1,4-dihydroquinol-4-one 3-carboxylic acid
6,8-difluoro-7-(4-carboxyphenyl)-1-ethyl-1,4-dihydroquinol-4-one 3-carboxylic acid.
6,8-difluoro-7-(3-chloro-4-hydroxyphenyl)-1-ethyl-1,4-dihydroquinol-4-one 3-carboxylic acid
6,8-difluoro-7-(3-hydroxyphenyl)-1-ethyl-1,4-dihydroquinol-4-one 3-carboxylic acid
6,8-difluoro-7-(4-aminomethylphenyl)-1-ethyl-1,4-dihydroquinol-4-one 3-carboxylic acid
6,8-difluoro-7-(3-aminomethylphenyl)-1-ethyl-1,4-dihydroquinol-4-one 3-carboxylic acid
6,8-difluoro-7-(4-hydroxymethylphenyl)-1-ethyl-1,4-dihydroquinol-4-one 3-carboxylic acid
6,8-difluoro-7-(3-hydroxymethylphenyl)-1-ethyl-1,4-dihydroquinol-4-one 3-carboxylic acid
6,8-difluoro-7-(4-methylsulfinylphenyl)-1-ethyl-1,4-dihydroquinol-4-one 3-carboxylic acid
6,8-difluoro-7-(4-methoxyphenyl)-1-ethyl-1,4-dihydroquinol-4one 3-carboxylic acid
6,8-difluoro-7-(3-methylsulfonylphenyl)-1-ethyl-1,4-dihydroquinol-4-one 3-carboxylic acid
6,8-difluoro-7-(4-hydroxyphenyl)-1-methyl-1,4-dihydroquinol-4-one 3-carboxylic acid and
6,8-difluoro-7-(3-hydroxymethyl-4-hydroxy)-1-ethyl-1,4-dihydroquinol-4-one 3-carboxylic acid.

Specific preferred compounds wherein $R_2$ is hydrogen are 6-fluoro-7-phenyl-1-ethyl-1,4-dihydroquinol-4-one 3-carboxylic acid
6-fluoro-7-(4-aminophenyl)-1-ethyl-1,4-dihydroquinol-4-one 3-carboxylic acid
6-fluoro-7-(4-nitrophenyl)-1-ethyl-1,4-dihydroquinol-4-one 3-carboxylic acid
6-fluoro-7-(4-formamidophenyl)-1-ethyl-1,4-dihydroquinol-4-one 3-carboxylic acid
6-fluoro-7-(4-acetamidophenyl)-1-ethyl-1,4-dihydroquinol-4-one 3-carboxylic acid
6-fluoro-7-(4-(N-(N'N'-dimethylformamidino))phenyl)-1-ethyl-1,4-dihydroquinol-4-one 3-carboxylic acid
6-fluoro-7-(4-formylphenyl)-1-ethyl-1,4-dihydroquinol-4-one 3-carboxylic acid
6-fluoro-7-(4-hydroxymethylphenyl)-1-ethyl-1,4-dihydroquinol-4-one 3-carboxylic acid
6-fluoro-7-(3-hydroxymethylphenyl)-1-ethyl-1,4-dihydroquinol-4-one 3-carboxylic acid and
6-fluoro-7-(4-aminosulfonylphenyl)-1-ethyl-1,4-dihydroquinol-4-one 3-carboxylic acid.

Other preferred compounds of the invention are those wherein $R_2$ and Y when taken together have the formula

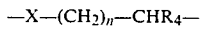

$$-X-(CH_2)_n-CHR_4-$$

wherein X is O, n is 1 and $R_4$ is methyl, e.g. 9-fluoro-10-(4-aminosulfonylphenyl)-3-methyl-7-oxo-2,3-dihydro-(7H)-pyrido-(1,2,3-de)-1,4-benzoxazine-6-carboxylic acid.

The present invention also relates to antibacterial compositions comprising an antibacterially acceptable carrier and a compound of formula I. Preferred compositions are those wherein the compound of formula I is a preferred compound as described above.

This invention further comprises a method of treating a host affected by a bacterial disease by administering to said host an antibacterially effective amount of a compound of formula I. Preferred methods of treatment are those administering a preferred compound of formula I as described above.

DETAILED DESCRIPTION OF THE INVENTION

The term "polyhaloalkyl" when used in the definition of $R_3$ means an alkyl having more than one halogen. Examples of such polyhaloalkyl groups are dichloromethyl, dibromoethyl, perfluoropropyl, etc.

The term "halo" or "halogen" whenever used in the claims and the description, e.g. in the definition of $R_3$, means fluoro, chloro, bromo or iodo.

According to a novel method described and claimed in copending application Ser. No. 679,146 filed Dec. 6, 1984, abandoned filed on the same date and assigned to the same assignee as the present application, the compounds of formula I are prepared by transition metal catalyst coupling of an appropriate arylmetallic compound containing group $R_3$ as defined above with the appropriate 7-$R_5$-quinolinone ester of the formula II

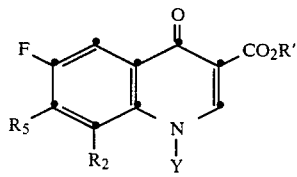

wherein $R_2$ and Y are as defined above, R' is alkyl of 1 to 6 carbon atoms and $R_5$ is bromo or iodo.

The coupling reaction is carried out in a reaction inert solvent, particularly an ethereal solvent such as a dialkylether, e.g. diethylether or dipropylether, dimethoxyethane, or cyclic ethers such as tetrahydrofuran (THF). A hydrocarbon may be present with the ether, particularly an aromatic or aliphatic hydrocarbon containing from 5 to 10 carbon atoms, e.g. benzene or toluene.

The arylmetallic compound may be made by methods known in the art, some of which are as described below.

The arylmetallic compound may be prepared from the corresponding halide of formula $R_3 R_5$ in which $R_3$ and $R_5$ are as defined above by direct lithium-halogen exchange using n-butyl, sec-butyl or t-butyl lithium followed by transmetallation by a wide variety of salts by known methods such as described by E. Negishi, Organometallics in Organic Synthesis, Vol. 1, page 104. The salts used are selected from salts of zinc, cadmium, magnesium, mercury, tin, silver, copper, and aluminum, preferably zinc. The most commonly used salts are the halides, particularly chlorides, bromides and iodides, and cyanides such as copper cyanide. The most advantageous salt is zinc chloride.

The above treatment with a butyllithium compound is best carried out in tetrahydrofuran at $-78°$ to $-50°$ C., preferably $-78°$ C. Other suitable solvents besides THF are ethereal solvents alone or in admixture with an aliphatic or aromatic hydrocarbon solvent having from 5 to 10 carbon atoms such as benzene or toluene. Examples of suitable ethers are dialkylethers such as diethylether or dipropylether, dimethoxyethane and cyclic ethers.

The arylmetallic compounds of use in the above process may also be prepared by direct reaction of the corresponding arylhalide with a metal in the zerovalent state. These metals are alkali metals such as lithium, sodium and potassium, alkaline earth metals such as magnesium and transition metals such as zinc. The solvents of use in this process are dialkylethers such as diethylether, cyclic ethers such as THF and dioxane, aliphatic or aromatic hydrocarbons having from 5 to 10 carbon atoms such as benzene and toluene or mixtures thereof containing at least 1 equivalent of the above ethers. The reaction temperatures vary from $-100°$ C., for reaction with very active metals, to 100° C.

Alternatively, the arylmetallic compounds may be formed by hydrogen-metal exchange between the corresponding aryl compound and a strong base such as potassium t-butoxide-butyllithium or TMEDA-butyllithium, or lithium or potassium hexamethyldisilizane.

The arylmetallic compound is coupled with the appropriate 7-$R_5$-quinolinone ester of formula II in the presence of 0.5–10 mole % of a transition metal catalyst at reaction temperatures generally ranging from room temperature to 50° C.

The transition metal catalysts are known, e.g. from Negishi, E., Acc. Chem. Res., 15, 340–348 (1982) and references cited therein. Suitable transition metals are platinum, cobalt, iron, zirconium, molybdenum, ruthenium, manganese, rhodium, preferably, nickel, palladium and platinum. These metals are combined with ligands such as $PPh_3$, $P(CH_3)_3$, and $P(C_2H_5)_3$, wherein Ph is phenyl. Preferred transition metal catalysts are $(PPh_3)_4Pd$, $(PPh_3)_2PdCl_2$, $(PPh_3)_4Ni$ and $(PPh_3)_2NiCl_2$. For the preparation of those compounds wherein $R_2$ and Y are taken together to form a tricyclic compound, (PPh$_3$)$_2$NiCl$_2$ is preferred.

Methods for preparation of the compounds of formula II are analogous to those described in the art. The overall reactions of two prior art methods are set out in reaction Schemes A and B hereafter.

In Scheme A, an aniline of formula IV wherein R$_2$ and R$_5$ are as defined above is reacted with a dialkyl alkoxymethylene malonate of formula V wherein R' is an alkyl group of 1 to 6 carbon atoms. The reaction is generally carried out without solvent at about 100° to 200° C., preferably 150° to 175° C., for about 0.5 to 24 hours, usually for 0.5 to 2 hours. The resulting intermediates of formula VI are crystallized from a hydrocarbon or ethereal solvent such as light petroleum or diethyl ether and cyclized by heating at about 150° to 250° C. in high boiling solvents such as dichlorobenzene, tetralin, diphenylether or diethyleneglycol dimethylether, preferably Dowtherm A which is a commercially available high boiling solvent mixture of diphenylether and dibenzofuran. The reaction time ranges from about 0.5 to 12 hours.

The intermediates of formula VII formed above are N-substituted with a halide Y-Hal wherein Y is as defined above and Hal is halogen. Examples of suitable halides are ethyliodide, 2-fluoro-1-iodoethane, allylbromide and 2-bromoethanol. The adduct formed on reaction with 2-bromoethanol may be converted to a compound of formula I wherein Y is vinyl by hydroxyl activation with e.g. thionyl chloride followed by elimination with a suitable base such as triethylamine, diazabicycloundecene and diazabicyclononane. Generally, the substitution is carried out in DMF with an inorganic base such as potassium carbonate at temperatures ranging from room temperature to 110° C.

The mono- or di-fluoro anilines of formula IV, also used in the reaction of Scheme B hereafter, may be prepared by conventional nitration and reduction methods such as disclosed by March, J., Adv. Org. Chem., Second Ed., McGraw Hill, 474, 1125 (1977) from the corresponding fluorobenzenes which are commericallly available.

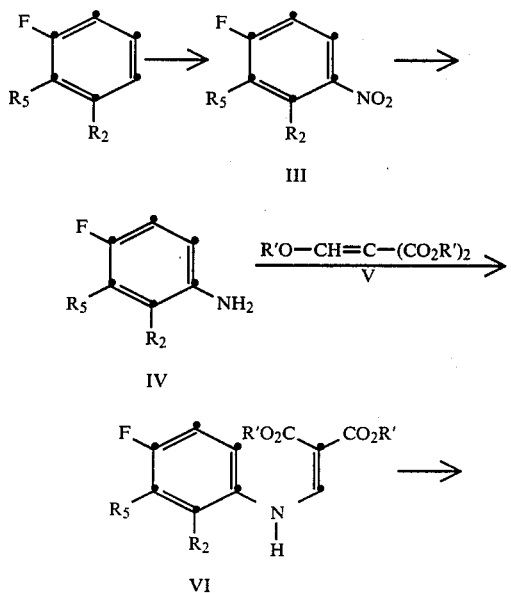

Scheme A

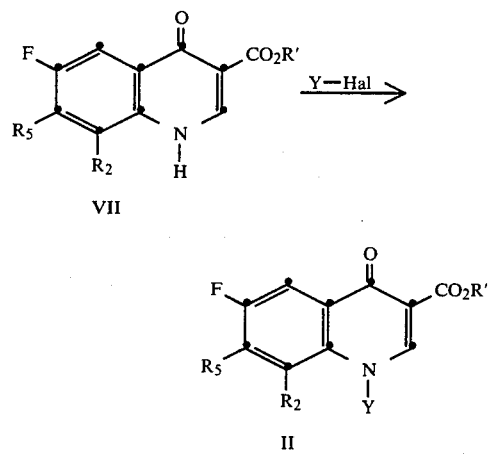

-continued
Scheme A

In Scheme B, an aniline of formula X wherein R$_2$, R$_5$ and Y are as defined above is reacted with a dialkyl alkoxymethylene malonate of formula V wherein each R' is alkyl having 1 to 6 carbon atoms or benzyl. The reaction conditions are as described above with reference to the conversion of compounds IV into V in Scheme A.

The cyclization of compound XI formed above is by heating in an acidic medium such as polyphosphoric acid at about 100° to 250° C. for about 0.5 to 24 hours, preferably at 100° to 150° C. for 0.5 to 2 hours. This procedure is described by Albrecht, R., Prog. Drug Res., Vol. 21, 35–49 (1977). The resulting ester of formula II is usually purified by recrystallization or chromatography.

The compounds of formula X may be prepared from those of formula IV by conventional methods. For instance, in Scheme B, an aniline of formula IV may be reacted with acetic anhydride in ethanol at about 25° to 100° C. The formed compound of formula VIII is reacted with a suitable base such as sodium hydride and N-substituted with an appropriate halide, tosylate or mesylate containing group Y. The acetyl group in the formed compound of formula IX is removed by refluxing in aqueous medium such as 6N hydrochloric acid to form the compound of formula X.

Alternatively, N-substituted anilines of formula X may be formed by reductive amination with an appropriate aldehyde and a suitable reducing agent such as diborane, palladium on carbon with hydrogen, sodium borohydride or sodium cyanoborohydride as for instance described in the above March reference, pages 819–820,

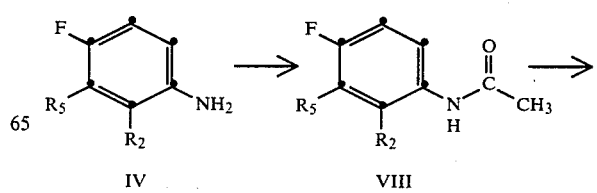

Scheme B

-continued
Scheme B

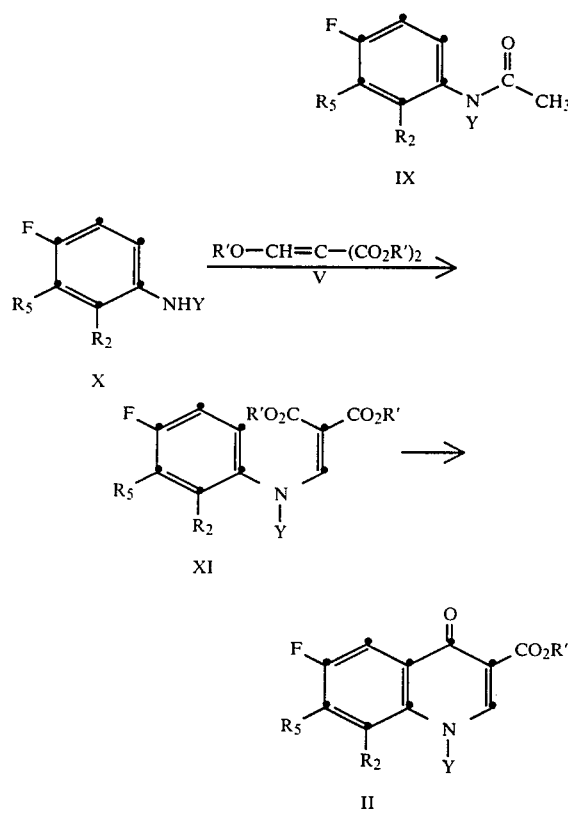

or by acylation of said aniline of formula IV by reaction with the appropriate anhydride or acid chloride and direct reduction to anilines X with diborane in THF.

The initial N-substitution of formula IV in Scheme B, rather than the later one of compounds of formula VII in Scheme A, is particularly useful when Y is polyfluoroalkyl since substitution with polyfluoroalkyl halides is not a viable route.

The intermediates of formula II wherein $R_2$ and Y are taken together to form tricyclic compounds are prepared by the methods of Schemes C to H hereafter.

The initial compound used in these methods is 2,4-difluoro-3-bromo-1-nitrobenzene formed from 1,3-difluoro-2-bromobenzene by conventional nitration such as described in the above March reference, pages 474–476.

Scheme C shows the preparation of tricyclic intermediates of formula XVII having a five-membered third ring in which $R_4$ is as defined above.

SCHEME C

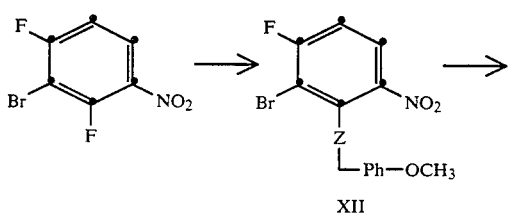

-continued
SCHEME C

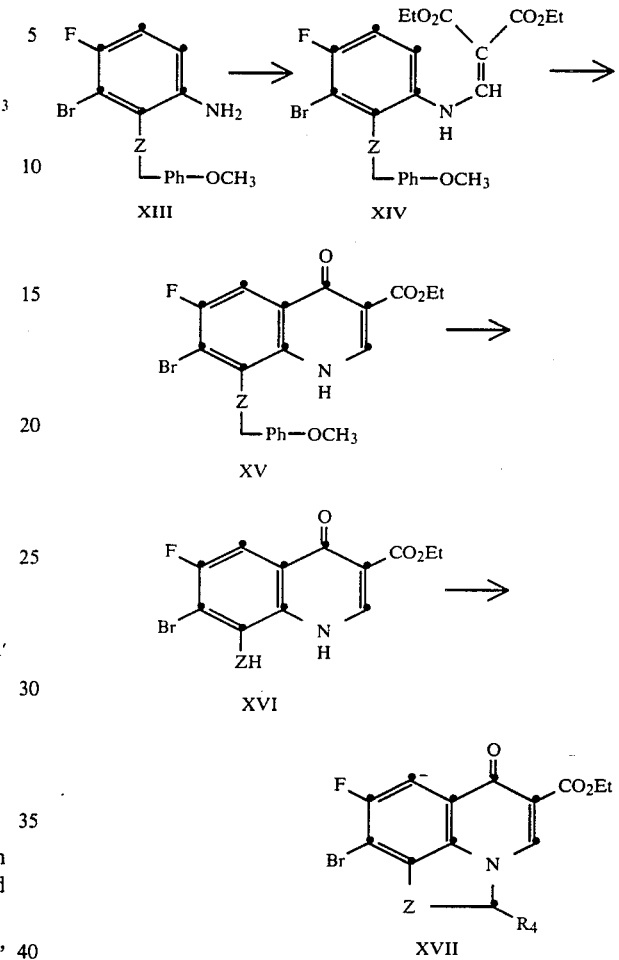

2-4-Difluoro-3-bromonitrobenzene is reacted with a reagent of the formula

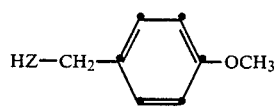

wherein Z is sulfur, oxygen, NH or $NCH_3$, in a polar organic solvent such as THF. When Z is sulfur, the reaction requires the presence of an organic base such as triethylamine. When Z is oxygen, a base such as sodium hydride is required for the reaction. Triethylamine, pyridine or another base is required when Z is NH or $NCH_3$ when only one equivalent of the above reagent is used.

The compound of formula XII is selectively reduced to the corresponding aniline by catalytic hydrogenation or by chemical reduction such as with stannous chloride in ethanol. After condensation of XIII with diethylethoxymethylene malonate at about 150° C., the compound of formula XIV is formed. Ring cyclization of XIV is by heating with e.g. Dowtherm A as the solvent. The substituted benzyl group is removed under acidic conditions e.g. with trifluoromethanesulfonic acid, trifluoroacetic acid and anisole.

The third ring is formed by reaction of XVI with R$_4$CHI$_2$ or R$_4$CHO wherein R$_4$ is as defined above to provide the compound of formula XVII.

Scheme D shows the preparation of tricyclic intermediates of formula XXIII wherein n is 0, 1 or 2, Z is S, NH or NCH$_3$, and R$_4$ is as defined above.

SCHEME D

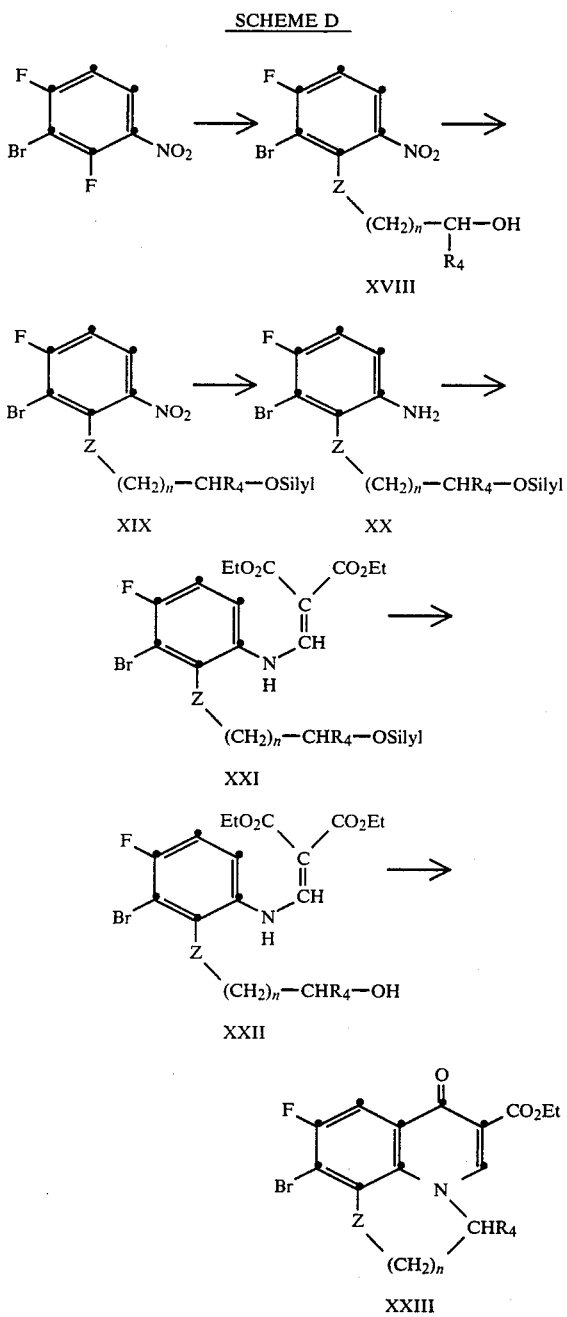

2,4-Difluoro-3-bromonitrobenzene is reacted with a compound of the formula HZ-(CH$_2$)n-CHR$_4$-OH wherein Z is S, NH or NCH$_3$ and n is 1 or 2, in a polar solvent such as THF at 0° C. to room temperature. When Z is S, a base is needed such as triethylamine. The compound of formula XVIII is reacted with a compound providing a protecting group such as a silyl group, specifically t-butyldimethylsilyl chloride, usually in DMF and imidazole, to form the compound of formula XIX. The next sequence of steps is the same as described with reference to Scheme B. Thus, there is hydrogenation of the nitro group and condensation with diethylethoxymethylene malonate. The compound of formula XXI is treated with fluoride to remove the protecting silyl group and cyclization is attained, after first reacting XXII with triphenylphosphine and ethylazodicarboxylate to close the second ring, by heating with polyphosphoric acid or ester at about 120° to 150° C. for 0.5 to 2 hours. "Silyl" is a trialkyl silyl group of the formula

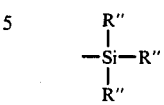

wherein R" is independently an alkyl group of 1–4 carbon atoms.

In Scheme E is illustrated the preparation of tricyclic intermediates of formula XXIX wherein n and R$_4$ are as defined above. 2,4-Difluoro-3-bromonitrobenzene is reacted with a monoprotected diol of formula Silyl-O-(CH$_2$)n-CHR$_6$-OH and a base like sodium hydride in THF at 0° C. to room temperature to give a compound of formula XXIV. In a sequence

SCHEME E

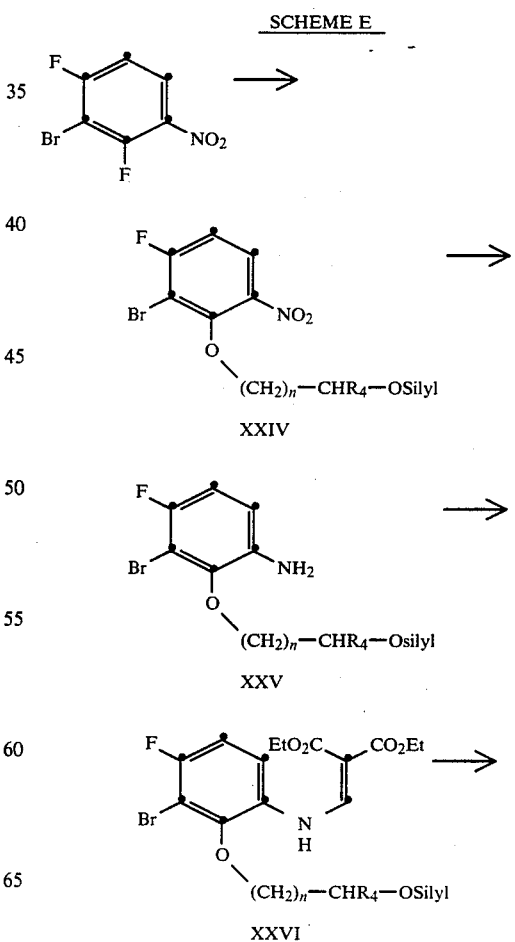

-continued
SCHEME E

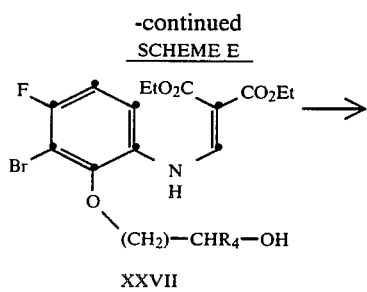

XXVII

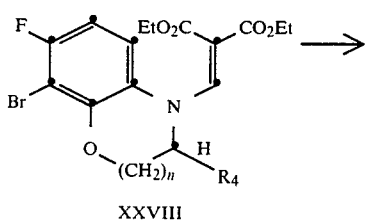

XXVIII

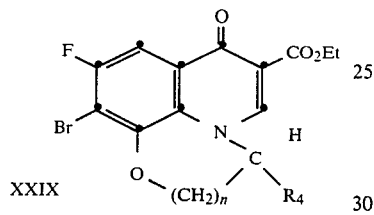

XXIX identical to that of Scheme D, intermediate XXIV is converted to XXIX by reduction of the nitro group, condensation with ethoxymethylene malonate to give XXVI, deprotection with fluoride, cyclization of the second ring with triphenylphosphine and ethyl azodicarboxylate and cyclization to the tricyclic compound with polyphosphate acid or ester at 120° C. to 150° C. for 0.5 to 2 hours.

Scheme F illustrates other methods for synthesis of tricycles of formula XXIX. Difluoro-3-bromonitrobenzene is reacted either directly with a hydroxyketone $HO(CH_2)_nC(O)R_4$ wherein $R_4$ and n are as defined above or first with potassium hydroxide in DMSO to give phenol XXX and then with an haloketone $X(CH_2)_nC(O)R_4$ with $R_4$ and n as defined above and X halogen to give common intermediate XXXI. The compound XXXI undergoes reductive cyclization to give benzoxazine XXXII. The compound XXXII is then condensed with ethoxymethylene malonate and cyclized in polyphosphate acid or ester using conditions described above to provide tricycle XXIX.

Schemes G and H illustrate the synthesis of tricyclic intermediates wherein Z is $CH_2$, and $R_4$ and n are as defined above.

SCHEME F

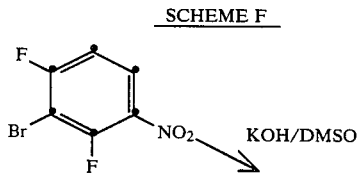

-continued
SCHEME F

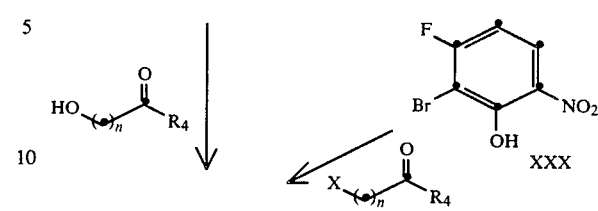

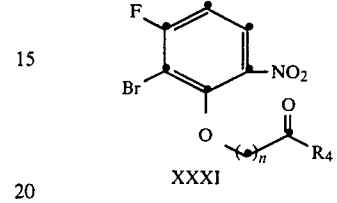

XXXI

↓ Ra/Ni

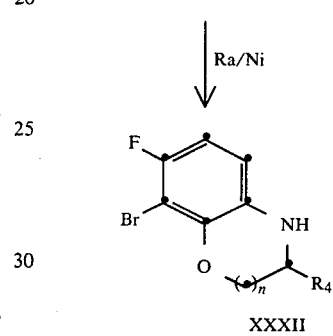

XXXII

↓

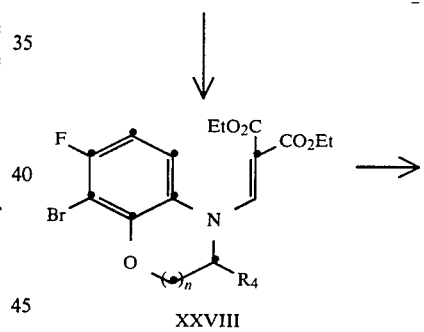

XXVIII

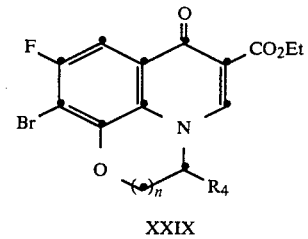

XXIX

SCHEME G

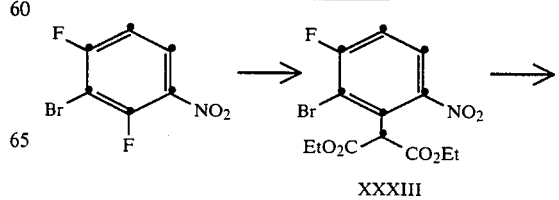

XXXIII

-continued
SCHEME G

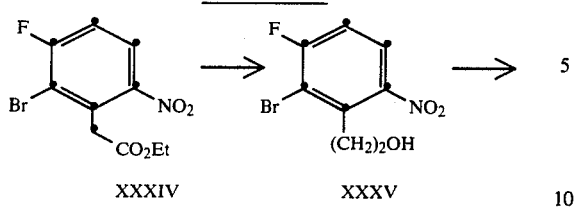

XXXIV → XXXV

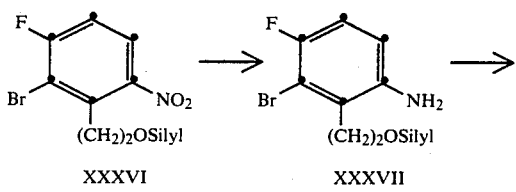

XXXVI → XXXVII

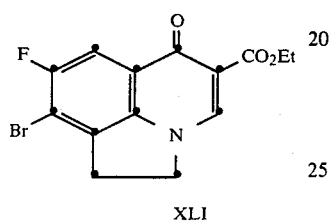

XLI

Scheme G illustrates the synthesis of tricyclic intermediates of formula XLI having a five-membered third ring. 2,4-Difluoro-3-bromonitrobenzene is reacted with diethylsodiomalonate in THF at 0° C. to room temperature to give intermediate XXXIII. Monodecarboxylation is effected with para-toluene sulfonic acid in THF and water at 80° C. The resulting ester XXXIV is reduced with diborane in THF at 50° C. for 48 hours. Protection of the alcohol with a "silyl" protecting group and reduction of the nitro group with Raney-Nickel in ethanol gives intermediate aniline XXXVII. Through the identical sequence of steps described in Schemes D, E and F, the tricyclic compound XLI is formed.

In Scheme H is illustrated the preparation of tricyclic intermediates of formula XLIX having six and seven-membered third rings wherein $R_4$ is as defined above and n is 1 or 2. Using intermediate XXXVII from Scheme G, the silyl group is removed and the hydroxyl group in resulting compound XXXVII is activated by reaction with para-toluene sulfonyl chloride in $CH_2Cl_2$ and pyridine. Addition of either one or two carbon atoms is accomplished by reaction of XLII (wherein Ts is p-toluenesulfonyl) with KCN, the anion of dithioacetal

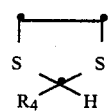

or the anion of $R_4$-functionalized diethyl malonate

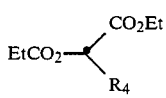

wherein $R_4$ is as defined above. The resulting

Scheme H

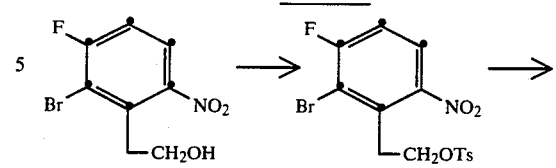

XXXVII → XLII

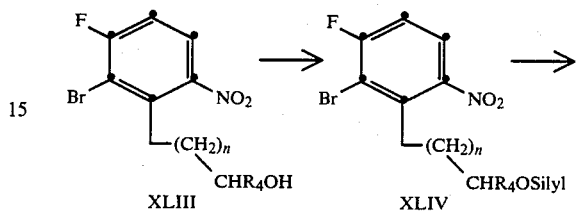

XLIII → XLIV

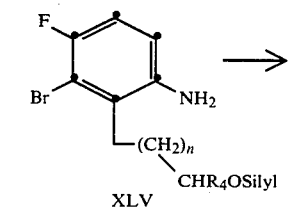

XLV

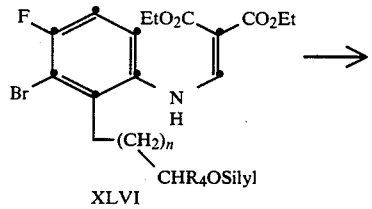

XLVI

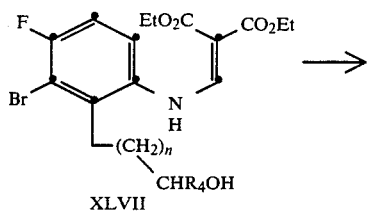

XLVII

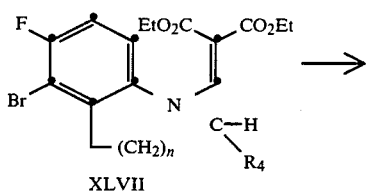

XLVII

XLIX intermediates of carbanion addition are subjected to hydrolysis, decarboxylation if necessary, and reduction by standard methods to give intermediate XLIII wherein n is 1 or 2. "Silyl" protection, reduction of the nitro group to give aniline XLV and diethyl ethoxymethylene malonate condensation gives XLVI. The protecting group is removed by treatment with fluoride ion and the second and third rings are formed by triphenyl phosphine, ethyl azodicarboxylate and polyphosphoric acid or ester, respectively, to give intermediate XLIX wherein n is 1 or 2.

Compounds of formula I wherein $R_3$ is phenyl substituted by alkylsulfinyl or alkylsulfonyl may be obtained by conventional oxidation of the corresponding compounds wherein $R_3$ is phenylmercaptoalkyl. The compounds (I) wherein $R_3$ is hydroxyphenyl may be formed by reacting the corresponding compound wherein $R_3$ is methoxyphenol with an ether-cleaving reagent such as borontribromide or trimethylsilyliodide.

Compounds (I) wherein $R_3$ is hydroxymethylphenyl are conveniently prepared by reacting the corresponding compound wherein $R_3$ is trialkylsilyloxymethylphenyl wherein each alkyl has 1 to 4 carbon atoms with an ether-cleaving agent as described above. Compounds (I) wherein $R_3$ is nitrophenyl may be prepared by conventional nitration of compounds (I) wherein $R_3$ is phenyl. Reduction of such nitrophenyl compounds provides compounds wherein $R_3$ is aminophenyl. These aminophenyl compounds on alkylation with usual alkylating agents such as alkyl halides result in compounds (I) wherein $R_3$ is alkylaminophenyl or dialkylaminophenyl. Similarly, compounds (I) wherein $R_3$ is alkylaminoalkylphenyl and dialkylaminoalkylphenyl are prepared by alkylation of corresponding compounds wherein $R_3$ is aminoalkylphenyl.

Compounds (I) wherein $R_3$ is formamidophenyl may be formed by reacting compounds wherein $R_3$ is aminophenyl with formic acid or a formic acid derivative such as ethylformate. Compounds (I) wherein $R_3$ is alkanoylamino are formed by reacting corresponding compounds wherein $R_3$ is aminophenyl with an alkanoyl group containing reagent such as an acid chloride or anhydride, e.g. acetic anhydride.

Compounds (I) wherein $R_3$ is N,N-dimethylformamidinophenyl are formed by reacting compounds (I) wherein $R_3$ is aminophenyl with dimethylformamide dimethylacetal in toluene.

Aminosulfonyl-substituted phenyl compounds may be obtained by reacting compounds (I) wherein $R_3$ is chlorosulfonylphenyl with an amino group introducing reagent such as ammonia or an amine. The chlorosulfonyl group is introduced by reacting compounds wherein $R_3$ is phenyl with chlorosulfonic acid. Alkylation of the aminosulfonylphenyl compounds will result in compounds (I) wherein $R_3$ is alkylaminosulfonylphenyl or dialkylaminosulfonylphenyl. These latter compounds alternatively may be obtained by reacting compounds (I) wherein $R_3$ is chlorosulfonylphenyl with a monoalkyl amine or a dialkyl amine, respectively.

Compounds (I) wherein $R_3$ is formylphenyl may be prepared by oxidation of the corresponding compound wherein $R_3$ is hydroxymethylphenyl, e.g. by oxidation with oxalyl chloride in DMSO and triethylamine.

Compounds (I) wherein $R_3$ is ureidophenyl are formed by reacting compounds wherein $R_3$ is aminophenyl with alkali metal cyanate such as sodium cyanate.

Compounds (I) wherein $R_3$ is azidomethylphenyl are prepared by reacting compounds wherein $R_3$ is methanesulfonyloxymethylphenyl with an azide such as sodium azide.

Compounds (I) wherein $R_1$ is hydrogen are obtained by acid or base hydrolysis of the corresponding esters wherein $R_1$ is alkyl or benzyl, or by hydrogenolysis of corresponding compounds wherein $R_1$ is benzyl.

The pharmaceutically acceptable cation salts of the compounds of formula I may be prepared by conventional methods. For instance, the salts may be prepared by treating the compound of formula I in which $R_1$ is hydrogen with an aqueous solution of the desired pharmaceutically acceptable cation and evaporating the resulting solution to dryness, preferably under reduced pressure. Suitable pharmaceutically acceptable cation salts for this purpose include alkali metal salts such as potassium, sodium and lithium salts, alkaline earth metal salts such as calcium and magnesium salts, and the ammonium or organic amine salts, such as choline or diethanolamine salts.

The compounds of the invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 10-1000 ppm, preferably 10-300 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. Generally, compound (I) is dissolved in a pharmacutically acceptable liquid such as water which may contain buffers, preservatives, materials to make the solution isotonic, e.g. isotonic saline, or other materials known to those skilled in art. The reconstituted solution so prepared may be used for direct parenteral injection or may be added to a solution such as an I.V. solution for slow administration by infusion.

The invention also provides pharmaceutical compositions comprising an antibacterially effective amount of a compound of the formula (I) together with a pharmaceutically acceptable diluent or carrier.

The compounds of the invention can be administered to humans for the treatment of bacterial diseases by either the oral or parenteral routes, and may be administered orally at dosage levels of about 0.1 to 500 mg/kg/day, advantageously 0.5-200 mg/kg/day, and parenterally at dosage levels of about 50 to 500 mg/kg/day given in a single dose or up to 3 divided doses. Variations will necessarily occur depending on the weight and condition of the subject being treated and the particular route of administration chosen as will be known to those skilled in the art.

The invention yet further provides a method of treating an animal, including a human being, having a bacterial disease which comprises administering to the animal an antibacterially effective amount of a compound of the formula (I) or a pharmaceutical composition as defined above.

The antibacterial activity of the compounds of the invention is shown by testing according to the Steer's replicator technique which is a standard in vitro bacterial testing method described by E. Steers et al., Antibiotics and Chemotherapy, 9, 307(1959).

The following Examples illustrate the invention.

EXAMPLE 1

3-Bromo-2,4-difluoronitrobenzene

A. A mixture of 10 ml concentrated HNO$_3$ and 10 ml concentrated H$_2$SO$_4$ was added dropwise with cooling to a stirred solution of 30 g 2,6-difluorobromobenzene in 50 ml of concentrated sulfuric acid. The rate of addition was controlled such that the temperature of the mixture did not rise above 55° C. After the addition was complete the reaction mixture was allowed to stir at room temperature for 2 hours. It was then poured onto ice and the resulting solid was collected by filtration, washed with water and dried, yielding a pale yellow solid, m.p. 50°–51.5° C., 84% yield (31.2 g).

Anal.: Calcd. for C$_6$H$_2$BrF$_2$NO$_2$: C, 30.28; H, 0.85; Br, 33.57; F. 15.96; N, 5.89%. Found: C, 30.34; H, 0.98; Br, 33.81; F, 16.04; N, 5.81%.

3-Amino-2,6-difluorobromobenzene

B. A mixture of 31.2 g of 3-bromo-2,4-difluoronitrobenzene, 150 ml concentrated HCl and 150 g stannous chloride dihydrate was placed in a preheated oil bath at 60° C. A small quantity of diethyl ether was then added to bring about solution. After heating at 60° C. for 30 minutes, the mixture was cooled and then poured into 1500 ml ice/water. The solution was then basified to pH 13 using 30% aqueous sodium hydroxide while maintaining the temperature below 25° C. by external cooling. The mixture was extracted three times with chloroform and the combined organic extracts were washed with water. The organic phase was dried and evaporated to yield a white solid, m.p. 77°–78° C., yield 90.5% (24.7 g).

Ethyl 7-bromo-6,8-difluoro-4-hydroxyquinoline-3-carboxylate

C. A stirred mixture of 26 g of 3-amino-2,6-difluorobromobenzene and 27 g of diethyl ethoxymethylenemalonate was heated at 150° C. for 1 hour. After cooling, 100 ml of Dowtherm "A" (commercially available high boiling inert solvent mixture of diphenylether and dibenzofuran) was added and the mixture was heated under nitrogen at 260° C. for 1.5 hour. The mixture was cooled to room temperature and 200 ml of hexanes was added. The resulting precipitate was collected by filtration, washed with hexanes and dried to give a cream solid, m.p. 285° C., yield 78% (32.32 g).

Ethyl 7-bromo-6,8-difluoro-1-ethyl-1,4-dihydroquinol-4-one 3-carboxylate

D. A mixture of 32 g of ethyl 7-bromo-6,8-difluoro-4-hydroxyquinoline-3-carboxylate, 45.1 g iodoethane and 50 g of anhydrous potassium carbonate in 450 ml N,N-dimethylformamide was heated at 90° C. with stirring for 2 hours. The mixture was then cooled, poured into water and the resulting precipitate was collected by filtration and dried. This crude product was purified by eluting on a silica column with ethyl acetate/hexanes (60:40) which on isolation yielded white crystals, m.p. 153°–155° C., yield 86% (29.84 g).

Analysis: Calcd. for C14H12BrF2NO3: C, 46.66; H, 3.33; N, 3.88%. Found: C, 46.38; H, 3.37; N, 3.87%.

Ethyl 6,8-difluoro-1-ethyl-7-phenyl-1,4-dihydroquinol-4-one 3-carboxylate ($R_1$=ethyl, $R_2$=F, $R_3$=phenyl, Y=ethyl)

E. A 2.7M solution (1 ml) of phenyllithium in 60/30 cyclohexane/diethyl ether was diluted with 10 ml dry tetrahydrofuran. This mixture was stirred under nitrogen at room tempeature and a solution of 409 mg anhydrous zinc chloride in 10 ml tetrahydrofuran was added. After 20 minutes, a solution of 360 mg of ethyl 7-bromo-6,8-difluoro-1-ethyl-1,4-dihydroquinol-4-one 3-carboxylate in 10 ml tetrahydrofuran and 124 mg of palladium tetrakis(triphenyl phosphine) were added. The resulting mixture was heated at 40°–45° C. for 18 hours. The mixture was then cooled and poured into 200 ml water. The mixture was stirred for 20 minutes and then extracted three times with chloroform. The organic extracts were combined, washed with water, dried and evaporated to give the crude product. This material was purified by eluting on a silica column with ethyl acetate which on isolation yielded the pure product as a solid (251 mg, 70% yield). NMR (CDCl3, 60 MHz): 8.4 (s, 1H), 8.1 (dd, 1H, J=9 Hz and 2 Hz), 7.5 (s, 5H), 4.4 (m, 4H), 1.5 (t, 3H, J=6.5 Hz), 1.4 (t, 3H, 6.5 Hz).

MS: Calcd. for C20H17F2NO3: 357.1178; Found: 357.1164.

6,8-Difluoro-1-ethyl-7-phenyl-1,4-dihydroquinol-4-one 3-carboxylic acid ($R_1$=H; $R_2$=F; $R_3$=phenyl; Y=ethyl). F. Ethyl 6,8-difluoro-1-ethyl-7-phenyl-1,4-dihydroquinol-4-one 3-carboxylate (186 mg) was dissolved in 10 ml 1:4 hydrochloric acid/acetic acid and the mixture was heated at reflux for 3.5 hours. The mixture was cooled and the resulting precipitate collected by filtration, washed with water and dried, yielding solid product, m.p. >260° C. (114 mg, 66% yield). NMR (DMSO-d6, 250 MHz): 8.75 (s, 1H), 7.9 (dd, 1H, J=9 Hz and 2 Hz), 7.35 (s, 5H), 4.5 (m, 2H), 1.35 (t, 3H, J=6.5 Hz). MS: Calcd. for C18H13F2NO3: 329.0864. Found: 329.0860.

Anal.: Calcd. for C18H13F2NO3.2/3H2O: C, 63.34; H, 4.00; N, 4.10%. Found: C, 63.08; H, 4.02; N, 4.14%.

EXAMPLE 2

Ethyl 6,8-difluoro-1-ethyl-7-(4-methylthiophenyl)1,4-dihydroquinol-4-one 3-carboxylate ($R_1$=ethyl; $R_2$=F; $R_3$=4-methylthiophenyl; Y=ethyl)

12.5 Ml of a 2M solution of t-butyllithium in pentane was added dropwise to a stirred solution of 2.53 g 4-bromothioanisole in 35 ml of dry tetrahydrofuran at −78° C. under nitrogen. After stirring for 1 hour at −78° C., a solution of 1.7 g anhydrous zinc chloride in 25 ml of tetrahydrofuran was added and the mixture was stirred for a further 15 minutes at −78° C. To the resulting solution, 620 mg of palladium tetrakis(triphenylphosphine) was added, followed by the slow addition of a solution of 1.8 g of ethyl 7-bromo-6,8-difluoro-1-ethyl-1,4-dihydroquinol-4-one 3-carboxylate in 10 ml tetrahydrofuran. After the addition was complete, the mixture was stirred for a further 15 minutes at −78° C. and then allowed to warm slowly to room temperature. After a further 24 hours, 5 ml of 5% aqueous ammonium chloride was added followed by 5 ml of 1M hydrochloric acid. The mixture was stirred for 10 minutes and it was then poured into 200 ml water and extracted with three 50 ml portions of chloroform. The combined organic extracts were washed once with water, dried and evaporated to yield the crude product as a yellow solid. This was purified by eluting on a silica column with ethyl acetate which on isolation gave the required product (1.7 g, yield 55%). NMR (CDCl3, 60 MHz); 8.35 (s, 1H), 8.05 (dd, 1H, J=9 Hz and 2 Hz), 7.35 (m, 4H), 4.35 (2q, 4H, J=6.5 Hz), 2.6 (s, 3H), 1.5 (t, 3H, J=6.5 Hz), 1.4 (t, 3H, J=6.5 Hz).

MS: Calcd. for C21H15F2NO3S: 403.1054; Found: 403.1031.

EXAMPLE 3

Ethyl 6,8-difluoro-1-ethyl-7-(4-methylsulfinylphenyl)-1,4-dihydroquinol-4-one 3-carboxylate ($R_1$=ethyl; $R_2$=F, $R_3$=4-methylsulfinylphenyl; Y=ethyl)

A. A solution of 101 mg 85% m-chloroperbenzoic acid in 3 ml dichloromethane was added dropwise to a stirred solution of 201 mg of ethyl 6,8-difluoro-1-ethyl-7-(4-methylthiophenyl)-1,4-dihydroquinol-4-one 3-carboxylate in dichloromethane at room temperature. After 1.5 hour, the reaction mixture was washed twice with 10 ml 5% aqueous sodium bicarbonate and the organic phase was dried and evaporated to give the crude required product as an oil. This was purified by elution on silica gel, first with ethyl acetate and then using a gradient elution with ethyl acetate/methanol. The product was a hard glass (90 mg, yield 43%). NMR (CDCl3, 60 MHz): 8.4 (s, 1H), 8.1 (dd, 1H, J=9 Hz and 2 Hz), 7.7 (m, 4H), 4.4 (2q, 4H, J=6.5 Hz), 2.8 (s, 3H), 1.5 (t, 3H, J=6.5 Hz), 1.4 (t, 3H, J=6.5 Hz).

6,8-Difluoro-1-ethyl-7-(4-methylsulfinylphenyl)-1,4-dihydroquinol-4-one 3-carboxylic acid ($R_1$=H; $R_2$=F; $R_3$=4-methylsulfinylphenyl; Y=ethyl)

B. 60 Mg (72% yield) was prepared from 90 mg ethyl 6,8-difluoro-1-ethyl-7-(4-methylsulfinylphenyl)-1,4-dihydroquinol-4-one 3-carboxylate by the method of Example 1F. White solid was obtained, m.p. >260° C. NMR (DMSO-d6, 250 MHz); 9.07 (s, 1H), 8.1 (dd, 1H, J=9 Hz and 2 Hz), 7.87 (m, 4H), 4.65 (m,2H), 2.85 (s, 3H), 1.5 (t, 3H, J=6 Hz).

MS: Calcd. for C19H15F2NO4S: 391.0690. Found: 391.0621. Anal.: Calcd. for C19H15F2NO4S: C, 58.31; H, 3.83; N, 3.58%. Found: C, 57.89; H, 4.15; N, 3.36%.

EXAMPLE 4

4-Fluoro-3-phenylnitrobenzene

A. 2-Fluoro-5-nitroaniline (30 g) was added portionwise over 45 minutes to a refluxing solution of 60 ml isoamyl nitrite in 225 ml benzene. After heating for a further 30 minutes at reflux, the mixture was cooled and the solvent removed by evaporation in vacuo. The residue was triturated many times with hot petroleum ether and the combined extracts were evaporated to give the product as a red oil (19.9 g, yield 49%). This material was used without further purification. NMR (CDCl3, 60MHz): 8.0–8.4 (m, 3H), 7.1–7.6 (m, 5H).

4-Fluoro-3-phenylaniline

B. A mixture of 18.5 g of 4-fluoro-3-phenylnitrobenzene, 76.7 g of stannous chloride dihydrate and 150 ml concentrated hydrochloric acid was heated at 60° C. for 2 hours with stirring. After cooling, the resulting precipitate was dissolved in water and the mixture was basified with sodium carbonate. The mixture was extracted five times with chloroform and the combined organic extracts were dried and evaporated to yield the product as a pale brown oil (10.9 g, yield 68%) which was used without further purification. NMR (CDCl3, 60 MHz): 7.15 (m, 5H), 7.1–6.1 (m, 3H), 3.3 (br,s, 2H).

Diethyl 4-fluoro-3-phenylanilinomethylenemalonate

C. A mixture of 10.9 g of 4-fluoro-3-phenylaniline and 12.54 g diethyl ethoxymethylenemalonate was heated at 150° C. for 15 minutes. The mixture was then cooled and triturated with petroleum ether to give the solid product (16.73 g, 80% yield) which was used without further purification. NMR (CDCl3, 60 MHz): 8.3 (d, 1H, J=14 Hz), 7.5–6.9 (m, 8H) 4.2 (m, 4H), 1.4 (m, 6H).

Ethyl 6-fluoro-7-phenylquinolin-4-ol 3-carboxylate

D. A solution of 16.73 g of diethyl 4-fluoro-3-phenylanilinomethylenemalonate in 100 ml Dowtherm "A" was heated at 250° C. with stirring for 2.5 hours. The mixture was cooled and the resulting precipitate was collected by filtration, washed with petroleum ether and dried, m.p. >270° C. (12.37 g, 85% yield). NMR (trifluoroacetic acid-d, 60 MHz); 9.3 (s, 1H), 8.2 (m, 2H), 7.5 (m, 5H), 4.7 (q, 2H, J=6.5 Hz), 1.5 (t, 3H, J=6.5 Hz).

Ethyl 1-ethyl-6-fluoro-7-phenyl-1,4-dihydroquinol-4-one 3-carboxylate ($R_1$=ethyl; $R_2$=H; $R_3$=phenyl; Y=ethyl)

E. A mixture of 12.4 g ethyl 6-fluoro-7-phenylquinolin-4-ol 3-carboxylate, 11 g anhydrous potassium carbonate and 18.7 g iodoethane in 100 ml N,N-dimethyl formamide was heated at 80° C. for 4 hours. The reaction mixture was cooled, poured into ethyl acetate and the mixture was extracted several times with water. The organic phase was dried and evaporated to give a solid product which was washed well with diethyl ether and dried. White solid was obtained, m.p. 180°–182° C. (9.16 g, 68% yield). NMR (CDCl3, 60 MHz); 8.4 (s, 1H), 8.05 (d, 1H, J=10 Hz), 7.5 (m, 6H), 4.3 (q, 2H, J=6.5 Hz), 4.25 (q, 2H, J=6.5 Hz), 1.55 (t, 3H, J=6.5 Hz), 1.35 (t, 3H, J=6.5 Hz).

1-Ethyl-6-fluoro-7-phenyl-1,4-dihydroquinol-4-one 3-carboxylic acid ($R_1$=$R_2$=H; $R_3$=phenyl; Y=ethyl).

F. A mixture of 0.44 g ethyl 1-ethyl-6-fluoro-7-phenyl1,4-dihydroquinol-4-one 3-carboxylate and 10 ml 1M sodium hydroxide was stirred at 90° C. for 1 hour. The mixture was cooled and poured into 20 ml water. The pH was adjusted to 7 with 1M hydrochloric acid and the resulting precipitate was collected by filtration, washed with water, then ether, and dried, yielding a white solid, m.p. 253°–256° C. (0.26 g, 65% yield). NMR (Trifluoroacetic acid-d, 60 MHz): 9.4 (s, 1H), 8.3 (m, 2H), 7.6 (m, 5H), 4.9 (q, 2H, J=6.5 Hz), 1.8 (t, 3H, J=6.5 Hz).

Anal.: Calcd for C18H14FNO3.1.5H2O: C, 63.90: H, 5.02; N, 4.14%. Found: C, 63.52; H, 4.66; N 3.92%.

EXAMPLE 5

Ethyl 1-ethyl-6-fluoro-7-(4-nitrophenyl)-1,4-dihydroquinol-4-one 3-carboxylate ($R_1$=ethyl; $R_2$=H; $R_3$=4-nitrophenyl; Y=ethyl)

A. Ethyl 1-ethyl-6-fluoro-7-phenyl-1,4-dihydroquinol-4-one 3-carboxylate (4 g) was added portionwise to a stirred mixture of 12 ml concentrated sulphuric acid and 12 ml concentrated nitric acid at 0° C. After 1 hour at 0° C., the mixture was poured onto ice and the resulting precipitate was collected by filtration. This solid was washed with ethyl acetate and then recrystallized from hot ethyl acetate to give a solid, m.p. 210°-212° C. (2.88 g, 68% yield). NMR (Trifluoroacetic acid-d, 250 MHz): 9.5 (s, 1H), 8.5 (m,4H), 8.0 (m, 2H), 5.05 (q, 2H, J=6.5 Hz), 4.75 (q, 2H, J=6.5 Hz), 1.85 (t, 3H, J=6.5 Hz), 1.5 (t, 3H, J=6.5 Hz). MS: 384 (parent), 312 (base peak).

1-Ethyl-6-fluoro-7-(4-nitrophenyl)-1,4-dihydroquinol-4-one 3-carboxylic acid ($R_1$=H; $R_2$, $R_3$ and Y as in Example 5A)

B. A mixture of 0.65 g of ethyl 1-ethyl-6-fluoro-7-(4-nitrophenyl)-1,4-dihydroquinol-4-one 3-carboxylate and 15 ml 1M sodium hydroxide was heated at 90° C. with stirring for 30 minutes. The mixture was cooled and then poured into 40 ml water. The pH of the mixture was adjusted to 7 with 1M hydrochloric acid and the resulting precipitate was collected by filtration. The solid was washed with water, ether and ethyl acetate and then it was recrystallized from hot N,N-dimethylformamide to give a white solid, m.p. >270° C. (0.29 g, 48% yield). NMR (Trifluoroacetic acid-d, 60 MHz): 9.5 (s, 1H), 8.5-7.7 (m, 6H), 5.1 (q, 2H), 1.85 (t, 3H).

EXAMPLE 6

Ethyl 1-ethyl-6-fluoro-7-(4-aminophenyl)-1,4-dihydroquinol-4-one 3-carboxylate ($R_1$=Y=ethyl; $R_2$=H; $R_3$=4-aminophenyl A. A mixture of 1.7 g of ethyl 1-ethyl-6-fluoro-7-(4-nitrophenyl)-1,4-dihydroquinol-4-one 3-carboxylate, 12.75 g stannous chloride dihydrate and 13 ml concentrated hydrochloric acid were stirred at 0° C. for 15 minutes and then at room temperature for 2 hours. The mixture was cooled and the resulting precipitate was collected by filtration, dissolved in water and the solution was adjusted to pH 9 with solid sodium bicarbonate. It was then extracted several times with ethyl acetate and then chloroform. The combined organic extracts were washed with water, dried and evaporated to give a white solid, m.p. 248°-250° C. (1.25 g, 78% yield). NMR (DMSO-d6, 250 MHz); 8.7 (s, 1H), 7.9 (d, 1H, J=11.5 Hz), 7.75 (d, 1H, J=6 Hz), 7.4 (dd, 2H, J=9 Hz), 6.7 (d, 2H, J=9 Hz), 4.5 (q, 2H, J=6.5 Hz), 4.25 (q, 2H, J=6.5 Hz), 1.45 (t, 3H, J=6.5 Hz), 1.3 (t, 3H, J=6.5 Hz).

1-Ethyl-6-fluoro-7-(4-aminophenyl)-1,4-dihydroquinol-4-one 3-carboxylic acid ($R_1$=$R_2$=H; $R_3$=4-aminophenyl; Y=ethyl)

B. A mixture of 0.8 g ethyl 1-ethyl-6-fluoro-7-(4-aminophenyl)-1,4-dihydroquinol-4-one 3-carboxylate and 16 ml 2M hydrochloric acid were heated at reflux for 6 hours. The mixture was cooled and the resulting precipitate was washed with water and dried to give the product as a yellow solid, m.p. 270°-272° C. (0.59 g, 78% yield). NMR (Trifluoroacetic acid-d, 250 MHz): 9.55 (s, 1H), 8.6 (d, 1H, J=8.5 Hz), 8.45 (d, 1H, J=6 Hz), 8.0 (d, 2H, J=9.5 Hz), 7.85 (d, 2H, J=9.5 Hz), 5.1 (m, 2H), 1.9 (t, 3H). MS: 326 (parent), 282 (base peak). Anal.: Calcd. for C18H15FN2O2.2.5H2O: C, 58.22; H, 5.39; N, 7.54%. Found: C, 58.25; H, 4.73; N, 7.44%.

EXAMPLE 7

1-Ethyl-6-fluoro-7-(4-formamidophenyl)-1,4-dihydroquinol-4-one 3-carboxylic acid ($R_1$=$R_2$=H; $R_3$=4-formamidophenyl; Y=ethyl).

1-Ethyl-6-fluoro-7-(4-aminophenyl)-1,4-dihydroquinol-4-one 3-carboxylic acid (100 mg) in 1 ml formic acid was heated at reflux for 5 hours. The mixture was cooled and the solvent removed by evaporation in vacuo. The residual solid was washed with water and diethyl ether and dried, yielding the product as a pale yellow solid, m.p. >270° C. (86 mg, 79% yield). NMR (DMSO-d6/Trifluoroacetic acid-d, 250 MHz): 9.4 (s, 1H), 8.5 (s, 0.5H), 8.4 (d, 1H, J=9 Hz), 8.3 (d, 1H, J=6 Hz), 8.2 (s, 0.5H), 7.9 (d, 2H, J=8 Hz), 7.8 (d, 2H, J=8 Hz), 5.0 (q, 2H, J=6.5 Hz), 1.75 (t, 3H, J=6.5 Hz). Anal.: Calcd. for C19H15FN2O4.1.5H2O: C, 59.84; H, 4.72, N, 7.35%. Found: C, 60.24; H, 4.31; N, 7.08%.

EXAMPLE 8

1-Ethyl-6-Fluoro-7-(4-acetamidophenyl)-1,4-dihydroquinol-4-one 3-carboxylic acid ($R_1$=$R_2$=H; $R_3$=4-acetamidophenyl; Y=ethyl)

1-Ethyl-6-fluoro-7-(4-aminophenyl)-1,4dihydroquinol-4-one 3-carboxylic acid (50 mg) was placed in a mixture of 1 ml acetic acid and 0.5 ml acetic anhydride and the mixture was stirred at room temperature for 1.5 hours. The resulting precipitate was collected by filtration washed with water and ether and dried, yielding the product as a white solid of m.p. >250° C. (35 mg, 62% yield). NMR (Trifluoroacetic aci d, 250 MHz): 9.5 (s, 1H), 8.55 (d, 1H, J=9 Hz), 8.4 (d, 1H, J=6 Hz), 7.85 (d, 2H, J=6 Hz), 7.75 (d, 2H, J=6 Hz), 5.05 (m, 2H), 2.55 (s, 3H), 1.85 (t, 3H, J=6 Hz).

EXAMPLE 9

1-Ethyl-6-fluoro-7-(N-(N',N'-dimethylformamidinophenyl)1,4-dihydroquinol-4-one 3-carboxylic acid ($R_1$=$R_2$=H; $R_3$=N-(N',N'-dimethylformamidinophenyl); Y=ethyl)

A mixture of 1-ethyl-6-fluoro-7-(4-aminophenyl)-1,4-dihydroquinol-4-one 3-carboxylic acid (100 mg) and N,N-dimethylformamide dimethylacetal (74 mg) in toluene was heated at reflux for 3 hours. A further 38 mg of N, N-dimethylformamide dimethylacetal was then added and the mixture was heated at reflux for a further 2 hours. The mixture was cooled, the solvent removed by evaporation in vacuo and the residual solid was washed with ether and dried, yielding the product as a pale yellow solid of m.p. 215°-218° C. (70 mg, 57% yield). NMR (DMSO-d6/Trifluoroacetic acid d, 250 MHz): 9.2 (s, 1H), 8.5(s, 1H), 8.3 (d, 1H, J=9 Hz), 8.15 (d, 1H, J=6 Hz), 7.85 (d, 2H, J=6 Hz), 7.6 (d, 2H, J=6 Hz). 4.8 (m, 2H), 3.45 (d, 6H, J=18 Hz), 1.65 (t, 3H, J=6 Hz). MS: 381 (66%).

Anal.: Calcd. for C21H20FN3O3: C, 63.16; H, 5.51; N, 10.52%. Found: C, 62.94; H, 5.25; N, 9.94%.

EXAMPLE 10

Ethyl 1-ethyl-6-fluoro-7-(4-chlorosulfonylphenyl)-1,4-dihydroquinol-4-one 3-carboxylate A. Chlorosulfonic acid (10 ml) was slowly added over 15 minutes to a stirred solution of ethyl 1-ethyl-6-fluoro-7-phenyl-1,4-dihydroquinol-4-one 3-carboxylate (2.5 g) in dichloromethane (20 ml) at 0° C. The mixture was stirred for a further 15 minutes at 0° C. and then at room temperature for 1.5 hour. The mixture was poured into ice/water and the mixture was extracted twice with ethyl acetate. The combined organic extracts were dried and evaporated to give the product as an oily solid (1.4 g, 42% yield) which was used immediately without further purification. NMR (CDCl3, 60 MHz): 8.6 (s, 1H), 8.4–7.4 (m, 6H), 4.4 (2q, 4H, J=6.5 Hz), 1.6 (t, 3H, J=6.5 Hz), 1.4 (t, 3H, J=6.5 Hz).

Ethyl
1-ethyl-6-fluoro-7-(4-aminosulfonylphenyl)-1,4-dihydroquinol-4-one 3-carboxylate ($R_1$=ethyl; $R_2$=H; $R_3$=4-aminosulfonylphenyl; Y=ethyl)

B. A saturated ethanolic ammonia solution (1 ml) was added to a stirred solution of ethyl 1-ethyl-6-fluoro-7-(4-chlorosulfonylphenyl)-1,4-dihydroquinol-4-one 3-carboxylate (0.7 g) in 8 ml dichloromethane at −50° C. The mixture was allowed to warm slowly to room temperature. After 2 hours, the mixture was poured into water and the resulting precipitate was collected by filtration, washed with water, ethyl acetate and ether and dried, yielding the product as a white solid (0.4 g, 60% yield). NMR (DMSO-d6, 60 MHz): 8.7 (s, 1H), 8.2–7.4 (m, 6H), 4.5 (q, 2H, J=6.5 Hz), 4.3 (q, 2H, J=6.5 Hz), 1.5 (t, 3H, J=6.5 Hz), 1.4 (t, 3H, J=6.5 Hz).

1-Ethyl-6-fluoro-7-(4-aminosulfonylphenyl)-1,4-dihydroquinol-4-one 3-carboxylic acid ($R_1$=H; $R_2$, $R_3$ and Y as in Example 10 B)

C. A mixture of 0.4 g ethyl 1-ethyl-6-fluoro-7-(4-aminosulfonylphenyl)-1,4-dihydroquinol-4-one 3-carboxylate, 5 ml ethanol and 5 ml 1M sodium hydroxide was heated at 90° C. for 30 minutes. The mixture was cooled, then concentrated in vacuo and the pH was adjusted to 7 with 1M hydrochloric acid. The resulting precipitate was collected by filtration, washed and dried to give the product as a white solid, m.p. >270° C. (0.3 g, 78% yield). NMR (DMSO-d6/Trifluoroacetic acid-d, 250 MHz): 9.45 (s, 1H), 8.5 (d, 1H, J=9 Hz), 8.4 (d, 1H, J=6 Hz), 8.2 (d, 2H, J=6.5 Hz), 7.95 (d, 2H, J=6.5 Hz), 5.0 (q, 2H), 1.8 (t, 3H, J=6.5 Hz).

Anal.: Calcd. for C18H15FN2O5S.0.5H2O: C, 54.10; H, 4.01; N, 7.01%. Found: C, 53.59; H, 4.00; N, 6.71%.

EXAMPLE 11

Ethyl
6,8-Difluoro-7-(3-methoxyphenyl)-1-ethyl-1,4-dihydroquinol-4-one 3-carboxylate A. 471 mg (60% yield) was prepared by the method of Example 2 using 935 mg of 1-bromo-3-methoxybenzene, 5 ml 2M t-butyl lithium solution, 818 mg anhydrous zinc chloride, 720 mg ethyl 7-bromo-6,8-difluoro-1-ethyl-1,4-dihydroquinol-4-one 3-carboxylate and 248 mg tetrakis(triphenylphosphine) palladium. NMR (CDCl3, 60 MHz): 8.4 (s, 1H), 8.1 (dd, 1H, J=9 and 2 Hz), 7.6−6.9 (m, 4H), 4.4 (2q, 4H, J=6.5 Hz), 3.8 (s, 3H), 1.5 (t, 3H, J=6.5 Hz), 1.4 (t, 3H, J=6.5 Hz).

MS: Calcd. for C21H19F2NO4: 387.1285. Found: 387.1267.

6,8-Difluoro-7-(3-methoxyphenyl)-1-ethyl-1,4-dihydroquinol-4-one 3-carboxylic acid B. 327 mg (76% yield) was prepared by the method of Example 1F from 471 mg ethyl 6,8-difluoro-7-(3-methoxyphenyl)-1-ethyl-1,4-dihydroquinol-4-one 3-carboxylate and recovered as a white solid of m.p. >260° C. NMR (DMSO-d6, 250 MHz): 9.05 (s, 1H), 8.05 (dd, 1H, J=9 Hz and 2 Hz), 7.5 (t, 1H), 7.15 (m, 2H), 4.65 (m, 2H), 3.85 (s, 3H), 1.45 (t, 3H, J=6 Hz).

MS: Calcd. for C19H15F2NO4: 359.0963. Found: 359.0979. Anal.: Calcd. for C19H15F2NO4: C, 63.50 H, 4.17; N, 3.89%. Found: C, 63.28; H, 4.14; N, 3.85%.

EXAMPLE 12

6,8-Difluoro-7-(3-hydroxyphenyl)-1-ethyl-1,4-dihydroquinol-4-one 3-carboxylic acid A solution of 292 mg 6,8-difluoro-7-(3-methoxyphenyl)-1-ethyl-1,4-dihydroquinol-4-one 3-carboxylic acid in 50 ml dichloromethane was stirred at −78° C. while 8.1 ml of 1M boron tribromide in dichloromethane was added dropwise. The reaction mixture was then allowed to warm slowly to room temperature and it was stirred overnight. The mixture was cooled to 5° C. and quenched with saturated aqueous sodium bicarbonate. The mixture was filtered and the filter residue was extracted with hot tetrahydrofuran. The organic extracts were evaporated to give a solid residue which was treated with 2M hydrochloric acid. The resulting solid was collected by filtration, washed with water and dried, yielding the required product as a white solid of m.p. >260° C. (217 mg, 77% yield). NMR (DMSO-d6, 250 MHz): 9.8 (s, 1H), 9.05 (s, 1H), 8.05 (dd, 1H, J=9 Hz and 2 Hz), 7.35 (t, 1H), 6.85 (m, 2H), 4.65 (m, 2H), 3.85 (s, 3H), 1.45 (t, 3H, J=6 Hz).

MS: Calcd. for C18H13F2NO4: 345.0913. Found: 345.0856. Anal.: Calcd. for C18H13F2NO4.0.5H2O: C, 61.01; H, 3.95; N, 3.95%. Found: C, 61.27; H, 3.95; N, 3.90%.

EXAMPLE 13

Ethyl
6,8-Difluoro-7-(4-methoxyphenyl)-1-ethyl-1,4-dihydroquinol-4-one 3-carboxylate A. 7.7 g of crude product was prepared by the method of Example 2 using 4.67 g of 1-bromo-4-methoxybenzene, 25 ml 2M t-butyl lithium solution, 3.75 g anhydrous zinc chloride, 7.2 g ethyl 7-bromo-6,8-difluoro-1-ethyl-1,4-dihydroquinol-4-one 3-carboxylate and 1.5 g tetrakis(triphenylphosphine) palladium. A pale yellow solid was recovered of m.p. 171°–172° C. NMR (CDCl3, 60 MHz): 8.3 (s, 1H), 8.0 (dd, 1H, J=9 HZ and 2 Hz), 7.6–6.9 (m, 4H), 4.4 (2q, 4H, J=6.5 Hz), 3.8 (s, 3H), 1.5 (t, 3H, J=6.5 Hz), 1.4 (t, 3H, J=6.5 Hz).

MS: Calcd. for C21H19F2NO4: 387.1279. Found: 387.1277.

6,8-Difluoro-7-(4-methoxyphenyl)-1-ethyl-1,4-dihydroquinol-4-one 3-carboxylic acid B. A mixture of 7.7 g of crude ethyl 6,8-difluoro-7-(4-methoxyphenyl)-1-ethyl-1,4-dihydroquinol-4-one 3-carboxylate, 50 ml tetrahydrofuran and 100 ml 1M hydrochloric acid was heated at reflux overnight. The reaction mixture was cooled and the resulting precipitate was collected by filtration, yielding the required product as a white solid (5.38 g, 75% yield) of m.p. 250°–252° C. NMR (Trifluoroacetic acid-d, 60 MHz): 9.2 (s, 1H), 8.1 (dd, 1H, J=9 Hz and 2 Hz), 7.4 (d, 2H, J=9 Hz), 7.0 (d, 2H, J=9 Hz), 4.8 (m, 2H), 3.9 (s, 3H), 1.6 (t, 3H, J=6.5 Hz).

MS: Calcd. for C18H15F2NO4: 359.0973. Found: 359.0986. Anal.: Calcd. for C18H15F2NO4.0.5H2O: C, 61.96; H, 4.35; N, 3.80%. Found: C, 61.78; H, 4.40; N, 3.60%.

EXAMPLE 14

6,8-Difluoro-7-(4-hydroxyphenyl)-1-ethyl-1,4-dihydroquinol-4-one 3-carboxylic acid A solution of 312 mg 6,8-difluoro-7-(4-methoxyphenyl)-1-ethyl-1,4-dihydroquinol-4-one 3-carboxylic acid in 40 ml dichloromethane was stirred at −78° C. while 8.69 ml of 1M boron tribromide in dichloromethane was added dropwise. The reaction mixture was then allowed to warm slowly to room temperature and it was stirred overnight. The mixture was cooled to 5° C. and quenched with saturated aqueous sodium bicarbonate. The mixture was extracted with dichloromethane and then several times with a mixture of tetrahydrofuran and ethyl acetate. The latter extracts were evaporated and the resulting solid was stirred with 1M hydrochloric acid for 30 minutes and the product was collected by filtration, washed with water and dried. The required product was a white solid (264 mg, 88% yield) of m.p. >270° C. NMR (DMSO-d6, 250 MHz): 9.05 (s, 1H), 8.0 (d, 1H, J=9 Hz), 7.4 (d, 2H, J=9 Hz), 6.95 (d, 2H, J=9 Hz), 4.65 (m, 2H), 1.45 (t, 3H, J=6 Hz).

MS: Calcd. for C18H13F2NO4: 345.0813. Found 345.0813. Anal.: Calcd. for C18H13F2NO4.H2O: C, 59.50; H, 4.13; N, 3.85%. Found: C, 59.59; H, 4.07; N, 3.74%.

EXAMPLE 15

4-Bromobenzyl dimethyl-t-butylsilyl ether

A. A mixture of 18.7 g 4-bromobenzyl alcohol, imidazole (13.6 g), dimethyl-t-butylsilyl chloride (15 g) and N,N-dimethylformamide (100 ml) was stirred at room temperature for 2 hours. The reaction mixture was poured into water and extracted three times with ether. The combined organic extracts was washed with water, brine and dried. Evaporation gave the product as a colorless oil (29.8 g, 99% yield) which was used without further purification. NMR (CDCl3, 250 MHz): 7.55 (d, 2H, J=9 Hz), 7.25 (d, 2H, J=9 Hz), 4.7 (s, 2H), 0.9 (s, 9H), 0.0 (s, 6H).

Anal.: Calcd. for C13H21BrOSi: C, 51.83; H, 6.97%. Found: C, 51.48; H, 6.93%.

Ethyl 1-ethyl-6,8-difluoro-7-(4-(dimethyl-t-butylsilyloxymethyl)-phenyl)-1,4-dihydroquinol-4-one 3-carboxylate B. 5.1 g (51% yield) was prepared by the method of Example 2 from 7.53 g of 4-bromobenzyl dimethyl-t-butylsilyl ether, 25 ml 2M t-butyl lithium solution, 3.75 g anhydrous zinc chloride, 7.2 g ethyl 7-bromo-6,8-difluoro-1-ethyl-1,4-dihydroquinol-4-one 3-carboxylate and 1.5 g tetrakis(triphenylphosphine) palladium. The title compound formed had a m.p. of 143°–144° C. NMR(DMSO-d6, 250 MHz): 8.7 (s, 1H), 7.95 (dd, 1H, J=9 and 2 Hz), 7.5 (q, 4H), 4.85 (s, 2H), 4.5 (br m, 2H), 4.25 (q, 2H), 1.45 (t, 3H, J=7 Hz), 1.4 (t, 3H, J=7 Hz), 0.95 (s, 9H), 0.15 (s, 6H).

Anal.: Calcd. for C27H33F2NO4Si: C, 64.67; H, 6.58; N, 2.79%. Found: C, 64.75; H, 6.72; N, 2.78%.

Ethyl 1-ethyl-6,8-difluoro-7-(4-hydroxymethylphenyl)-1,4-dihydroquinol-4-one 3-carboxylate C. A mixture of 5.1 g ethyl 1-ethyl-6,8-difluoro-7-(4-(dimethyl-t-butylsilyloxymethyl)-phenyl)-1,4-dihydroquinol-4-one 3-carboxylate and 10.2 ml of 1M tetra-n-butylammonium fluoride in tetrahydrofuran was stirred at room temperature for 2 hours. The reaction mixture was poured into water and extracted three times with ether and once with chloroform. The combined organic extracts were dried and evaporated to yield the product as a yellowish solid of m.p. 230°–232° C. (3.8 g, 96% yield). NMR (DMSO-d6, 250 MHz): 8.7 (s, 1H), 7.9 (dd, 1H, J=2 Hz and 10 Hz), 7.5 (s, 4H), 4.6 (d, 2H), 4.5 (m, 2H), 4.25 (q, 2H, J=6.5 Hz), 1.45 (t, 3H, J=6.5 Hz), 1.35 (t, 3H, J=6.5 Hz).

MS: Calcd. for C21H19F2NO4: 387.1279. Found 387.1275.

1-Ethyl-6,8-difluoro-7-(4-hydroxymethylphenyl)-1,4-dihydroquinol-4-one 3-carboxylic acid D. 600 mg (43% yield) was prepared by the method of Example 13B from 1.5 g ethyl 1-ethyl-6,8-difluoro-7-(4-hydroxymethylphenyl)-1,4-dihydroquinol-4-one 3-carboxylate as a white solid of m.p. 269° C. NMR (DMSO-d6, 250 MHz): 9.05 (s, 1H), 8.05 (dd, 1H, J=2 Hz and 9 Hz), 7.55 (s, 4H), 5.35 (t, 1H, J=4 Hz), 4.65 (m, 2H), 4.6 (d, 2H, J=4 Hz), 1.45 (t, 3H, J=6 Hz).

MS: Calcd. for C19H15F2NO4: 359.0965. Found: 359.0972. Anal.: Calcd. for C19H15F2NO4: C, 63.51; H, 4.18; N, 3.90%. Found: C, 63.15; H, 4.21; N, 3.66%.

EXAMPLE 16

3-Bromobenzyl dimethyl-t-butylsilyl ether

A. A mixture of 5.0 g 3-bromobenzyl alcohol, imidazole (3.64 g), dimethyl-t-butylchlorosilane (4.02 g) and N,N-dimethylformamide (25 ml) was stirred at room temperature for 2 hours. The reaction mixture was poured into water and extracted three times with ether. The combined organic extract was washed with water, brine and dried. Evaporation gave the product as a colorless oil (6.83 g, 85% yield) which was used without further purification.

Ethyl 1-ethyl-6,8-difluoro-7-(3-(dimethyl-t-butylsilyloxymethyl)-phenyl)-1,4-dihydroquinol-4-one 3-carboxylate B. 7.0 g (87% yield) was prepared by the method of Example 2 from 6.82 g of 3-bromobenzyl dimethyl-t-butylsilyl ether, 25 ml 2M t-butyl lithium solution, 3.4 g anhydrous zinc chloride, 5.9 g ethyl 7-bromo-6,8-difluoro-1-ethyl-1,4-dihydroquinol-4-one 3-carboxylate and 1.5 g tetrakis(triphenylphosphine) palladium. The melting point was 107°–109° C. NMR (DMSO-d6, 250 MHz): 8.7 (s, 1H), 7.92 (dd, 1H, J=9 and 2 Hz), 7.49 (m, 4H), 4.82 (s, 2H), 4.47 (m, 2H), 4.26 (q, 2H), 1.42 (t, 3H, J=7 Hz), 1.3 (t, 3H, J=7 Hz), 0.94 (s, 9H), 0.1 (s, 6H).

Anal.: Calcd. for C27H33F2NO4Si: C, 64.67; H, 6.58; N, 2.79%. Found: C, 64.51, H, 6.59; N, 2.75%.

Ethyl 1-ethyl-6,8-difluoro-7-(3-hydroxymethylphenyl)-1,4-dihydroquinol-4-one 3-carboxylate C. 4.2 g (78% yield) was prepared by the method of Example 15C from 7.0 g of ethyl 1-ethyl-6,8-difluoro-7-(3-(dimethyl-t-butylsilyloxymethyl)-phenyl)-1,4-dihydroquinol-4-one 3-carboxylate and 14 ml of 1M tetra-n-butylammonium fluoride in tetrahydrofuran. A yellow solid of m.p. 162°–166° C. was recovered. NMR (DMSO-d6, 250 MHz): 8.7 (s, 1H), 7.95 (dd, 1H, J=2 Hz and 9 Hz), 7.5 (m, 4H), 5.3 (t, 3H, J=6 Hz), 4.6 (d, 2H, J=6 Hz), 4.5 (m, 2H), 4.25 (q, 2H, J=6.5 Hz), 1.45 (t, 3H, J=6.5 Hz), 1.3 (t, 3H, J=6.5 Hz).

MS: Calcd. for C21H19F2NO4: 387.1279. Found: 387.1280.

1-Ethyl-6,8-difluoro-7-(3-hydroxymethylphenyl)-1,4-dihydroquinol-4-one 3-carboxylic acid D. 330 mg (92% yield) was prepared by the method of Example 13B from 387 mg ethyl 1-ethyl-6,8-difluoro-7-(3-hydroxymethylphenyl)-1,4-dihydroquinol-4-one 3-carboxylate as a white solid of m.p. 230°–231° C. NMR (DMSO-d, 250 MHz): 9.1 (s, 1H), 8.05 (dd, 1H, J=9 Hz and 2 Hz), 7.5 (m, 4H), 4.65 (m, 2H), 4.6 (s, 2H), 1.45 (t, 3 H, J=6 Hz).

Anal.: Calcd.: Cor C19H15F2NO4.0.5H2O: C, 61.95; H, 4.35; N, 3.80%. Found: C, 61.89; H, 4.50; N, 3.48%.

EXAMPLE 17

Ethyl 1-ethyl-6,8-difluoro-7-(4-azidomethylphenyl)-1,4-dihydroquinol-4-one 3-carboxylate A. A solution of 585 mg methanesulfonyl chloride in 20 ml dichloromethane was added dropwise to a stirred solution of 15 ml triethylamine and 1.8 g ethyl 1-ethyl-6,8-difluoro-7-(4-hydroxymethylphenyl)-1,4-dihydroquinol-4-one 3-carboxylate in 100 ml dichloromethane at 0° C. After the addition was complete, the reaction mixture was extracted with 120 ml water and the organic phase was dried and evaporated to yield the mesylate product which was used directly without further purification.

This mesylate was dissolved in acetone containing 605 mg sodium azide. Water was added dropwise until solution of the azide was complete. The reaction mixture was stirred overnight at room temperature. The reaction mixture was partitioned between water and dichloromethane and the aqueous phase was extracted twice more and the combined organic extracts were washed with water and brine and dried. Evaporation gave the crude product which was purified by elution on silica gel yielding pure product as a solid of m.p. 149.5°–150° C. (850 mg, 44% yield). NMR (DMSO-d6, 250 MHz): 8.7 (s, 1H), 7.95 (dd, 1H, J=2 Hz and 9 Hz), 7.6 (ABq, 4H), 4.6 (s, 2H), 4.5 (m, 2H), 4.25 (q, 3H), J=6.5 Hz), 1.45 (t, 3H, J=6.5 Hz), 1.35 (t, 3H, J=6.5 Hz).

MS: Calcd. for C21H18F2N4O3: 412.1343. Found: 412.1344.

Anal.: Calcd. for C21H18F2N4O3: C, 61,16; H, 4.37; N, 13.59%. Found: C, 61.65; H, 4.55; N, 13.13%.

Ethyl 1-ethyl-6,8-difluoro-7-(4-aminomethylphenyl)-1,4-dihydroquinol-4-one 3-carboxylate B. A solution of 2.6 g ethyl 7-(4-azidomethylphenyl)-1-ethyl-6,8-difluoro-1,4-dihydroquinol-4-one 3-carboxylate in 50 ml methanol and 100 ml chloroform, containing 1.3 g 5% palladium on charcoal was hydrogenated at 12 p.s.i. for 2 hours. The reaction mixture was filtered and the filtrate was evaporated. The residue was triturated with a small quantity of chloroform and dried, yielding 2.2 g of the product as a solid (92% yield), m.p. 262°–263° C. NMR (DMSO-d6, 250 MHz): 8.72 (s, 1H), 8.5 (br s, 2H), 7.95 (dd, 1H, J=2 and 9 Hz), 7.65 (q, 4H), 4.49 (br m, 2H), 4.3 (q, 2H), 4.13 (s, 2H), 1.42 (t, 3H, J=7 Hz), 1.3 (t, 3H, J=7 Hz).

MS: Calcd. for C21H20F2N2O3: 386.1437. Found: 386.1448.

1-Ethyl-6,8-difluoro-7-(4-aminomethylphenyl)-1,4-dihydroquinol-4-one 3-carboxylic acid hydrochloride salt C. 135 mg (79.3% yield) was prepared by the method of Example 13B from 450 mg ethyl 7-(4-aminomethylphenyl)-1-ethyl-6,8-difluoro-1,4-dihydroquinol-4-one 3-carboxylate. White solid of m.p. >280° C. NMR (DMSO-d6, 250 MHz): 9.1 (s, 1H), 8.1 (dd, 1H, J=2 Hz and 9 Hz), 7.7 (ABqt, 4H), 4.65 (m, 2H), 4.15 (s, 2H), 1.45 (t, 3H, J=6.5 Hz).

MS: Calcd. for C19H16F2N2O3: 358.1129. Found: 358.1169

Anal.: Calcd. for C19H16F2N2O3.HCl. 2H2O: C, 53.02; H, 4.88; N, 6.51%. Found: C, 53.66; H, 4.35; N, 6.60%.

EXAMPLE 18

Ethyl 1-ethyl-6,8-difluoro-7-(3-azidomethylphenyl)-1,4-dihydroquinol-4-one 3-carboxylate A. 2.28 g (54% yield) was prepared by the method of Example 17A using 1.3 g methanesulfonyl chloride in 25 ml dichloromethane, added to a solution of 25 ml triethylamine and 4.0 g ethyl 1-ethyl 6,8-difluoro-7-(3-hydroxymethylphenyl)-1,4-dihydroquinol-4-one 3-carboxylate in 100 ml dichloromethane at 0° C., followed by 5.36 g sodium azide in 150 ml acetone. The product formed was a solid of m.p. 119° C. NMR (DMSO-d6, 250 MHz): 8.7 (s, 1H), 7.9 (dd, 1H, J=2 Hz and 9 Hz), 7.55 (m, 4H), 4.6 (s, 2H), 4.5 (m, 2H), 4.25 (q, 2H, J=6.5 Hz), 1.45 (t, 3H, J=6.5 Hz), 1.3 (t, 3H, J=6.5 Hz).

MS: Calcd. for C21H18F2N4O3: 412.1343. Found: 412.1363.

Anal.: Calcd. for C21H18F2N4O3: C, 61.16; H, 4.37; N, 13.59%. Found: C, 61.27; H, 4.58; N, 12.77%.

Ethyl 1-ethyl-6,8-difluoro-7-(3-aminomethylphenyl)-1,4-dihydroquinol-4-one 3-carboxylate B. 200 mg (85% yield) was prepared by the method of Example 17B from 250 mg ethyl 1-ethyl-6,8-difluoro-7-(3-azidomethylphenyl)-1,4-dihydroquinol-4-one 3-carboxylate. A pale brown solid was formed, m.p. 260°–262° C. NMR (DMSO-d6, 250 MHz): 8.72 (s, 1H), 8.4 (br s, 2H), 7.97 (br d, 1H, J=9 Hz), 7.65 (m, 4H), 4.49 (br m, 2H), 4.27 (q, 2H), 4.12 (s, 2H), 1.45 (t, 3H, J=7 Hz), 1.32 (t, 3H, J=7 Hz).

MS: 386 (parent), 314 (base).

1-Ethyl-6,8-difluoro-7-(3-aminomethylphenyl)-1,4-dihydroquinol-4-one 3-carboxylic acid hydrochloride salt C. 135 mg (79.3% yield) was prepared by the method of Example 13B from 450 mg ethyl 1-ethyl-6,8-difluoro-7-(4-aminomethylphenyl-1,4-dihydroquinol-4-one 3-carboxylate. White solid of m.p. >280° C. NMR (DMSO-d6, 250 MHz): 9.1 (s, 1H), 8.1 (dd, 1H, J=2 Hz and 9 Hz), 7.65 (m, 4 H), 4.65 (m, 2H), 4.1 (s, 2H), 1.45 (t, 3H, J=6.5 Hz).

MS: Calcd. for C19H16F2N2O3: 358.1129. Found: 358.1172. Anal.: Calcd. for C19H16F2N2O3.HCl.1.5-H2O: C, 56.57; H, 4.46; N, 6.95%. Found: C, 56.80; H, 4.47; N, 6.99%.

EXAMPLE 19

3-(2-Fluorophenyl)-toluene

A. A 1.46M solution (45 ml) of toluylmagnesium bromide in ether was added to a mixture of 10 g 2-bromofluorobenzene and 250 mg bis(diphenylphosphinoethane)-nickel dichloride in 70 ml dry diethyl ether. The mixture was then heated at reflux for 18 hours. The mixture was cooled to room temperature and quenched with 10% aqueous ammonium chloride, followed by 1M hydrochloric acid, and then partitioned between ether and water. The aqueous phase was extracted once more with ether and the combined organic extracts were dried and evaporated yielding the crude product as an oil which was purified by elution from silica gel with hexanes. The product was a colorless oil (7.0 g, 66% yield) which was used without further purification. NMR (CDCl3, 60MHz): 7.4–6.9 (m, 8H), 2.4 (s, 3H).

3-(2-Fluorophenyl)-benzoic acid

B. A mixture of 7.0 g 3-(2-fluorophenyl)-toluene and 29.5 g potassium permanganate in 500 ml t-butanol and 100 ml water was heated at 90° C. for 18 hours. The reaction mixture was cooled to room temperature, sufficient sodium bisulfite was added to dissolve the remaining potassium permanganate and manganese dioxide, and the pH was adjusted to 1 with hydrochloric acid. The resulting precipitate was collected by filtration, redissolved in ethyl acetate and this solution was dried and evaporated yielding the product as a white solid of m.p. 147°–148° C. after recrystallization from hexanes (5.7 g, 70% yield). NMR (DMSO-d6, 250 MHz): 8.2–7.3 (m, 8H).

MS: Calcd. for $C_{13}H_9F_2O$: 216.0585. Found: 216.0585.

3-(2-Fluoro-5-nitrophenyl)-benzoic acid

C. A solution of 420 mg potassium nitrate in 5 ml concentrated sulfuric acid was added dropwise to a stirred solution of 1 g 3-(2-fluorophenyl)-benzoic acid in 25 ml concentrated sulfuric acid at 0° C. The mixture was stirred at 0° C. for 20 minutes and then poured into iced water. The resulting precipitate was extracted into ethyl acetate and the extracts were combined, dried and evaporated, yielding the product as a white solid (1.2 g, 100% yield), m.p. 272°–274° C. after recrystallization from ethyl acetate. NMR (DMSO-d6, 250 MHz): 8.4 (m, 2H), 8.16 (d, 1H, J=2 Hz), 8.05 (multiplets, 1H), 7.9 (multiplets, 1H), 7.66 (m, 2H), 3.4 (br s, 1H).

MS: Calcd. for $C_{13}H_8NF_4$: 261.0438. Found: 261.0416.

Anal.: Calcd. for $C_{13}H_8NF_4 \cdot 1/4H_2O$: C, 58.75; H, 3.20; N, 5.27%. Found: C, 58.84; H, 3.19; N, 5.12%.

3-(2-Fluoro-5-nitrophenyl)-benzyl alcohol

D. A 1M solution (200 ml) of diborane in tetrahydrofuran was added to a stirred solution of 3-(2-fluoro-5-nitrophenyl)-benzoic acid (6.6 g) in 500 ml tetrahydrofuran. The reaction mixture was stirred at room temperature for 12 hours and then quenched with water and extracted with ethyl acetate. The organic extracts were dried and evaporated to yield a yellow solid which was purified by elution on silica gel with 40% ethyl acetate/hexanes. This gave the pure required product as a yellow solid (4.04 g, 65% yield), m.p. 113°–114° C. NMR (CDCl3, 250 MHz): 8.42 (four line multiplet, 1H), 8.25 (8 line multiplet, 1H), 7.55 (m, 4H), 7.3 (four line multiplet, 1H), 4.8 (d, 2H, J=4.5 Hz), 0.9 (t, 1H).

MS: Calcd. for $C_{13}H_{10}FNO_3$: 247.0645. Found: 247.0647.

Anal.: Calcd. for $C_{13}H_{10}FNO_3$: C, 63.16; H, 4.05; N, 5.67%. Found: C, 63.42; H, 4.11; N, 5.53%.

3-(3-t-Butyldimethylsilyloxymethylphenyl)-4-fluoronitrobenzene

E. A mixture of 4.04 g 3-(2-fluoro-5-nitrophenyl)-benzyl alcohol, 2.23 g imidazole and 2.46 g t-butyldimethylsilylchloride in 100 ml N,N-dimethylformamide was stirred at room temperature for 30 minutes. The reaction mixture was then partitioned between water and ether. The combined organic extracts were washed three times with water, dried and evaporated yielding the product as a yellow oil (5.9 g, 99% yield) which was purified on silica gel to give a yellow solid of m.p. 44°–45° C. NMR (CDCl3, 250 MHz): 8.4 (dd, 1H), 8.34 (eight line multiplet, 1H), 7.5 (m, 4H), 7.3 (m, 1H), 4.83 (s, 2H), 0.95 (s, 9H), 0.15 (s, 6H).

Anal.: Calcd. for $C_{18}H_{21}FNO_3Si$: C, 63.16; H, 6.65; N, 3.88%. Found: C, 62.99; H, 6.62; N, 3.82%.

3-(3-t-Butyldimethylsilyloxymethylphenyl)-4-fluoroaniline

F. A solution of 5.92 g 3-(3-t-butyldimethylsilyloxymethylphenyl)-4-fluoronitrobenzene in 200 ml 50% ethyl acetate/hexanes was hydrogenated over 5 g of 5% palladium on carbon at 50 p.s.i. for 15 minutes. The reaction mixture was filtered and evaporated to yield the crude product (5.43 g, 100% yield) which was used directly without further purification. On purification, the compound is characterized by the following data: NMR (CDCl3, 250 MHz): 7.45 (m, 4H), 6.98 (dd, 1H), 6.75 (dd, 1H), 6.62 (8 line multiplet, 1H), 4.8 (s, 2H), 3.6 (br s, 2H), 0.95 (s, 9H), 0.01 (s, 6H).

MS: Calcd. for $C_{19}H_{29}FNOSi$; 331.1768. Found: 331.1776.

Anal.: Calcd. for $C_{19}H_{29}FNOSi$: C, 68.88; H, 7.86; N, 4.23%. Found: C, 69.15; H, 8.18; N, 4.14%.

Diethyl (3-(3-t-butyldimethylsilyloxymethylphenyl)-4-fluoronitroanilino)methylene malonate G. A mixture of 5.4 g 3-(3-t-butyldimethylsilyloxymethylphenyl)-4-fluoroaniline and 3.9 ml diethyl ethoxymethylenemalonate were heated at 150° C. for 15 minutes. The mixture was cooled and the resulting oil was purified by elution on silica gel with 25% ethyl acetate/hexanes to give the product as a clear pale green oil (90% yield). NMR (CDCl3, 250 MHz): 11.1 (d, 1H, J=9 Hz), 8.5 (d, 1H, J=9 Hz), 7.45 (m, 5H), 7.2 (m, 2H), 4.82 (s, 2H), 4.3 (m, 4H), 1.35 (m, 6H), 0.95 (s, 9H), 0.15 (s, 6H).

MS: Calcd. for $C_{27}H_{36}FNO_5Si$: 501.2346. Found: 501.2344.

Anal.: Calcd. for $C_{27}H_{36}FNO_5Si$: C, 64.67; H, 7.19; N, 2.79%. Found: C, 64.47; H, 7.06; N, 2.97%.

Ethyl 7-(3-t-butyldimethylsilyloxymethylphenyl)-6-fluoro-4-hydroxyquinoline 3-carboxylate H. A mixture of diethyl (3-(3-t-butyldimethylsilyloxymethylphenyl)-4-fluoronitroanilino)methylene malonate (2.4 g) in 18 ml Dowtherm A was heated at 260° C. for 2.5 hours. The reaction mixture was cooled and triturated with hexanes yielding the product as a white solid (1.13 g, 52% yield), m.p. 310°-312° C. with decomposition. NMR (1% DMSO-d6/TFA-d, 250 MHz): 9.4 (m, 1H), 8.38 (m, 2H), 7.83 (m, 2H), 7.65 (m, 2H), 5.55 (s, 2H), 5.0(s, 1H), 4.68 (q, 2H), 1.55 (t, 3H), 1.01 (s, 9H), 0.4 (s, 6H).

Ethyl 7-(3-t-butyldimethylsilyloxymethylphenyl)-1-ethyl-6-fluoro-1,4-dihydroquinol-4-one 3-carboxylate I. A mixture of 1.13 g ethyl 7-(3-t-butyldimethylsilyloxymethylphenyl)-6-fluoro-4-hydroxyquinoline 3-carboxylate, 3 ml iodoethane and 1.5 g potassium carbonate in 50 ml N,N-dimethylformamide was stirred at room temperature for 24 hours. The reaction mixture was partitioned between ethyl acetate and water. The ethyl acetate layer was washed four times with water and dried. Evaporation gave the crude product which was eluted on silica gel with ethyl acetate/hexanes to yield the pure product as a pale yellow oil (1.02 g, 85% yield). NMR (CDCl3, 250 MHz): 8.55 (s, 1H), 8.3 (d, 1H, J=11Hz), 7.5 (m, 5H), 4.85 (s, 2H), 4.45 (q, 2H, J=6.5 Hz), 4.3 (q, 3H, J=6.5 Hz), 1.6 (t, 3H, J=6.5 Hz), 1.45 (t, 3H, J=6.5 Hz), 1.0 (s, 9H), 0.0 (s, 6H).

Ethyl 1-ethyl-6-fluoro-7-(3-hydroxymethylphenyl)-1,4-dihydroquinol-4-one 3-carboxylate J. A 1M solution (2.11 ml) of tetra-n-butylammonium fluoride in tetrahydrofuran was added to a solution of 1.02 g ethyl 7-(3-t-butyldimethylsilyloxymethylphenyl)-1-ethyl-6-fluoro-1,4-dihydroquinol-4-one 3-carboxylate in 20 ml tetrahydrofuran. After 15 minutes, the solution was partitioned between ethyl acetate and water. The organic extracts were dried and evaporated to give the product as a white solid (755 mg, 97% yield).

1-Ethyl-6-fluoro-7-(3-hydroxymethylphenyl)-1,4-dihydroquinol-4-one 3-carboxylic acid K. A mixture of 755 mg ethyl 1-ethyl-6-fluoro-7(3-hydroxymethylphenyl)-1,4-dihydroquinol-4-one 3-carboxylate, 50 ml 1M sodium hydroxide and 5 ml tetrahydrofuran were heated at 90° C. for 30 minutes. The solution was cooled and acidified to pH 1 with 6M hydrochloric acid. The resulting precipitate was collected by filtration, washed with water and dried, yielding the product as a white solid of m.p. 203°-204° C. (587 mg, 84% yield). NMR (DMSO-d6, 250 MHz): 9.1 (s, 1H), 8.1 (m, 2H), 7.5 (m, 4H), 4.7 (q, 2H), 4.6 (d, 2H, J=.7 Hz), 1.45 (t, 3H, J=6.5 Hz).

MS: Calcd. for C19H16FN04: 341.1064. Found: 341.1060.

Anal.: Cald. for C19H16FN04.0.25H20: C, 65.99; H, 4.78; N, 4.05%. Found: C, 66.09; H, 5.16; N, 3.91%.

EXAMPLE 20

4-(2-Fluorophenyl)-toluene

A. 6.0 g (57% yield) was prepared as an oil by the method of Example 19A from 10 g 2-bromofluorobenzene, 250 mg bis(diphenylphosphinylethane)nickel dichloride and 89 ml 0.73M 4-toluylmagnesium bromide. The product was used without further purification. NMR (CDCl3, 60 MHz): 7.5—6.9 (m, 8H), 2.3 (s, 3H).

4-(2-Fluorophenyl)-benzoic acid

B. 1.17 g (100% yield) was prepared by the method of Example 19B from 1.0 g 4-(2-fluorophenyl)-toluene and a white solid of m.p. 226°-227° C. was recovered. NMR (DMSO-d6, MHz) 8.1 (d, 2H), 7.8—7.3 (m, 6H).

4-(2-Fluoro-5-nitrophenyl)-benzoic acid

C. 1.2 g (100% yield) was prepared by the method of Example 19C from 1.0 g 4-(2-fluorophenyl)-benzoic acid. White solid of m.p. >280° C. NMR (DMSO-d6, 250 MHz): 8.5—7.6 (m, 7H).

MS: Calcd. for C13H8NF04: 261.0438. Found: 261.0457.

4-(2-Fluoro-5-nitrophenyl)-benzyl alcohol

D. 700 mg (61% yield) was prepared by the method of Example 19D from 1.2 g 4-(2-fluoro-5-nitrophenyl)-benzoic acid. Pale yellow solid of m.p. 106°-108.5° C. NMR (CDCl3, 250 MHz): 8.4 (m, 1H), 8.2 (m, 1H), 7.55 (ABq, 4H), 7.3 (m, 1H), 4.8 (d, 2H, J=6 Hz).

3-(4-t-Butyldimethylsilyloxymethylphenyl)-4-fluoronitrobenzene

E. 6.0 g (98% yield) was prepared by the method of Example 19E from 4.2 g 4-(2-fluoro-5-nitrophenyl)benzyl alcohol, 2.5 g imidazole and 3.5 g t-butyldimethylsilyl chloride. The oil was used without further purification.

3-(4-t-butyldimethylsilyloxymethylphenyl)-4-fluoroaniline

F. 5.5 g was prepared by the method of Example 19F from 6.0 g 3-(4-t-butyl-dimethylsilyloxymethylphenyl)-4-fluoronitrobenzene. The formed oil was used without further purification.

Diethyl (3-(4-t-butyldimethylsilyloxymethylphenyl)-4-fluoroanilino)methylenemalonate G. 5.12 g (60% yield) was prepared by the method of Example 19G from 5.5 g 3-(4-t-butyldimethylsilyloxymethylphenyl)-4-fluoroaniline and 3.5 ml diethyl ethoxymethylenemalonate. A pale yellow-green oil was obtained. NMR (CDCl3, 250 MHz): 8.5 (d, 1H, J=12 Hz), 7.5 (ABq, 4H), 7.2 (m, 3H), 4.8 (s, 2H), 4.25 (m, 4H), 1.35 (m, 6H), 1.0 (s, 9H), 0.1 (s, 6H).

Ethyl 7-(4-t-butyldimethylsilyloxymethylphenyl)-6-fluoro-4-hydroxyquinoline 3-carboxylate H. 379 mg (42% yield) was prepared by the method of Example 19H from 1.0 g diethyl (3-(4-t-butyldimethylsilyloxymethylphenyl)-4-fluoroanilino)methylenemalonate. A white solid of m.p. >280° C. was recovered.

Ethyl 7-(4-t-butyldimethylsilyloxymethylphenyl)-1-ethyl-6-fluoro-1,4-dihydroquyinol-4-one 3-carboxylate I. 233 mg (58% yield) was prepared as a solid of m.p. 158°-160° C. by the method of Example 19I from 379 mg ethyl 7-(4-t-butyldimethylsilyloxymethylphenyl)-6-fluoro-4-hydroxyquinoline 3-carboxylate. NMR (CDCl3, 250 MHz): 8.5 (s, 1H), 8.2 (d, 1H, J=11 Hz), 7.5 (ABq, 4H), 7.45 (d, 1H), 4.8 (s, 2H), 4.4 (q, 2H, J=6.5 Hz), 4.3 (q, 2H, J=6.5 Hz), 1.55 (t, 3H, J=6.5 Hz), 1.4 (t, 3H, J=6.5 Hz), 1.0 (s, 9H), 0.1 (s, 6H).

Ethyl 1-ethyl-6-fluoro-7-(4-hydroxymethylphenyl)-1,4-dihydroquinol-4-one 3-carboxylate J. 170 mg (97% yield) was prepared by the method of Example 19J from 230 mg ethyl 7-(4-t-butyldimethylsilyloxymethylphenyl)-1-ethyl-6-fluoro-1,4-dihydroquinol-4-one 3-carboxylate as a white solid which was used without further purification.

1-Ethyl-6-fluoro-7-(4-hydroxymethylphenyl)-1,4-dihydroquinol-4-one 3-carboxylic acid K. 155 mg (95% yield) was prepared by the method of Example 19K from 170 mg ethyl 1-ethyl-6-fluoro-7-(4-hydroxymethylphenyl)-1,4-dihydroquinol-4-one 3-carboxylate. A white solid of m.p. 220°–221° C. was recovered after recrystallisation from dimethyl formamide. NMR (DMSO-d6, 250 MHz): 9.1 (s, 1H), 8.1 (dd, 2H), 8.6 (ABq, 4H), 4.7 (q, 2H), 4.6 (s, 2H), 1.45 (t, 3H, J=6.5 Hz).

EXAMPLE 21

Ethyl 1-ethyl-6-fluoro-7-(4-formylphenyl)-1,4-dihydroquinol-4-one 3-carboxylate A. Oxalyl chloride (171 mg) was added dropwise to a solution of ethyl 1-ethyl-6-fluoro-7-(4-hydroxymethylphenyl)-1,4-dihydroquinol-4-one 3-carboxylate (450 mg) in 8 ml dichloromethane and 2 ml dimethyl sulfoxide at −78° C. After 25 minutes, 0.9 ml triethylamine was added, the mixture warmed to room temperature and partitioned between water and ethyl acetate. The organic phase was dried and concentrated to a small volume. The product was precipitated by addition of diethyl ether as a white solid of m.p. 165°–170° C. (360 mg, 80% yield). NMR (CDCl3, 250 MHz): 10.1 (s, 1H), 8.55 (s, 1H), 8.3 (d, 1H, J=11 Hz), 8.0 (d, 2H, J=9 Hz), 7.75 (d, 2H, J=9 Hz), 7.5 (d, 1H, J=6 Hz), 4.4 (2q, 4H), 1.6 (t, 3H, J=6.5 Hz), 1.45 (t, 3H, J=6.5 Hz).

MS: Calcd. for C21H18NO4F: 367.1220. Found: 367.1230.

1-Ethyl-6-fluoro-7(4-formylphenyl)-1,4-dihydroquinol-4-one 3-carboxylic acid B. 63 mg (62% yield) was prepared by the method of Example 19K from 110 mg ethyl 1-ethyl-6-fluoro-7-(4-formylphenyl)-1,4-dihydroquinol-4-one 3-carboxylate as a white solid of m.p. >270° C.

NMR (DMSO-d6/Trifluoroacetic acid-d, 250 MHz): 9.45 (s, 1H), 8.5 (d, 1H, J=11 Hz), 8.4 (d, 1H, J=6 Hz), 8.2 (d, 2H, J=9 Hz), 8.0 (d, 2H, J=9 Hz), 5.0 (m, 2H), 1.8 (t, 3H, J=6.5 Hz).

MS: Calcd. for C19H14FNO4: 339.0908. Found: 339.0872.

Anal. Calcd. for C19H14FNO4: C, 67.26; H, 4.13; N, 4.13%. Found: C, 67.08; H, 4.45; N, 4.04%.

EXAMPLE 22

4-Bromo-2-chloroanisole

A. A solution of 4-bromo-2-chlorophenol (5.18 g) in 20 ml tetrahydrofuran was added dropwise to a stirred mixture of sodium hydride (0.72 g) in tetrahydrofuran (50 ml). After 30 minutes, iodomethane (4.26 g) was added and the mixture was stirred overnight at room temperature. A further 7.1 g of iodomethane was added and the mixture was heated at reflux overnight. The reaction mixture was then partitioned between water and chloroform. The combined organic extracts were dried and evaporated to yield the product after washing with hexanes as a white solid (5.4 g, 98% yield) of m.p. 63° C. Anal.: Calcd. for C7H6BrClO: C, 38.00; H, 2.71%. Found: C, 38.07; H, 2.80%.

Ethyl 1-ethyl-7-(3-chloro-4-methoxyphenyl)-6,8-difluoro-1,4-dihydroquinol-4-one 3-carboxylate B. 300 mg (35.5% yield) was prepared by the method of Example 2 using 1.11 g 4-bromo-2-chloroanisole, 5 ml 2M t-butyl lithium solution, 750 mg zinc chloride and 720 mg ethyl 7-bromo-6,8-difluoro-1-ethyl-1,4-dihydroquinol-4-one 3-carboxylate and 100 mg tetrakis(triphenylphosphine)palladium. A yellow solid of m.p. 280° C. was recovered.

NMR (CDCl3, 250 MHz): 8.45 (s, 1H), 8.15 (dd, 1H, J=2 Hz and 9 Hz), 7.55 (s, 1H), 7.4 (m, 1H), 7.1 (d, 1H, J=9 Hz), 4.4 (2q, 4H), 4.0 (s, 3H), 1.55 (t, 3H, J=6.5 Hz), 1.45 (t, 3H, J=6.5 Hz).

Anal.: Calcd. for C21H18ClF2NO4.0.5H20: C, 58.00; H, 4.41; N, 3.25%. Found: C, 59.06; H, 4.52; N, 3.17%.

7-(3-chloro-4-methoxyphenyl)-6,8-difluoro-1-ethyl-1,4-dihydroquinol-4-one 3-carboxylic acid C. 250 mg (90% yield) was prepared by the method of Example 13B from 300 mg of ethyl 1-ethyl-7-(3-chloro-4-methoxyphenyl)-6,8-difluoro-1,4-dihydroquinol-4-one 3-carboxylate. A white solid was recovered having a m.p. >280° C.

Anal.: Calcd. for C19H14ClF2NO4.1/3H20: C, 57.14; H, 3.67; N, 3.50%. Found: C, 57.16; H, 3.69; N, 3.22%. NMR (DMSO-d6, 250 MHz): 9.05 (s, 1H), 8.05 (dd, 1H, 9 Hz and 2 Hz), 7.7 (s, 1H), 7.55 (m, 1H), 7.35 (d, 1H, J=9 Hz), 4.65 (m, 2H), 3.95 (s, 3H), 1.45 (t, 3H, J=6.5 Hz).

EXAMPLE 23

7-(3-chloro-4-hydroxyphenyl)-6,8-difluoro-1-ethyl-1,4-dihydroquinol-4-one 3-carboxylic acid 40 mg (21% yield) was prepared by the method of Example 14 from 200 mg of 7-(3-chloro-4-methoxyphenyl)-6,8-difluoro-1-ethyl-1,4-dihydroquinol-4-one 3-carboxylic acid. Yellow solid of m.p. 235°–238° C.

NMR (DMSO-d6, 250 MHz): 9.05 (s, 1H), 8.05 (dd, 1H, J=2 Hz and 9 Hz), 7.65 (s, 1H), 7.4 (d, 1H, J=9 Hz), 7.15 (d, 1H, J=9 Hz), 4.65 (m, 2H), 1.45 (t, 3H, J=6.5 Hz).

MS: Calcd. for C18H12ClF2NO4: 379.0423. Found: 379.0423.

EXAMPLE 24

Ethyl 6,8-difluoro-1-ethyl-7-(2-methoxyphenyl)-1,4-dihydroquinol-4-one 3-carboxylate A. 504 Mg (65% yield) was prepared by the method of Example 2 using 935 mg of 2-bromoanisole, 5 ml 2M t-butyl lithium, 818 mg anhydrous zinc chloride, 720 mg ethyl 7-bromo-6,8-difluoro-1,4-dihydroquinol-4-one 3-carboxylate and 248 mg tetrakis(triphenylphosphine)palladium. NMR (CDCl3, 250 MHz): 8.4 (s, 1H), 8.0 (dd, 1H, J=2 Hz and 9 Hz), 7.2 (m, 4H), 4.4 (2q, 4H), 3.8 (s, 3H), 1.5 (t, 3H, J=6 Hz), 1.4 (t, 3H, J=6 Hz).

MS: Calcd. for C21H19F2NO4: 387.1285. Found: 387.1306.

6,8-Difluoro-1-ethyl-7-(2-methoxyphenyl)-1,4-dihydroquinol-4-one 3-carboxylic acid B. 343 Mg (74% yield) was prepared by the method of Example 1F from 500 mg ethyl 6,8-difluoro-1-ethyl-7-(2-methoxyphenyl)-1,4-dihydroquinol-4-one 3-carboxylate as a white solid of m.p. >260° C. Anal.: Calcd. for C19H15F2NO4.1H20: C, 60.47; H, 4.50; N, 3.71%. Found: C, 60.73; H, 4.17; N, 3.82%.

NMR (DMSO-d6, 250 MHz): 9.05 (s, 1H), 8.05 (dd, 1H, J=2 Hz and 9 Hz), 7.55 (m, 1H), 7.45 (d, 1H, J=9 Hz), 7.25 (d, 1H, J=9 Hz), 7.15 (m, 1H), 4.65 (m, 2H), 3.8 (s, 3H), 1.45 (t, 3H, J=6.5 Hz).

MS: Calcd. for C19H15F2NO4: 359.0969. Found: 359.0963.

EXAMPLE 25

6,8-Difluoro-1-ethyl-7-(2-hydroxyphenyl)-1,4-dihydroquinol-4-one 3-carboxylic acid 135 Mg (45% yield) was prepared by the method of Example 12 from 310 mg 6,8-difluoro-1-ethyl-7-(2-methoxyphenyl)-1,4-dihydroquinol-4-one 3-carboxylic acid. A cream solid of m.p. >260° C. was recovered. Anal. calcd. for C18H13F2NO4.1/4H20: C, 61.80; H, 3.71; N, 4.00%. Found: C, 61.54; H, 3.98; N, 3.91%.

NMR (DMSO-d6, 250 MHz): 10 (br s, 1H), 9.1 (s, 1H), 8.05 (dd, 1H, J=2 Hz and 9 Hz), 7.35 (m, 2H), 7.0 (m, 2H), 4.65 (m, 2H), 1.45 (t, 3H, J=6 Hz).

MS: Calcd. C18H13F2NO4: 345.0911. Found: 345.0911.

EXAMPLE 26

3-Bromo-4-fluoroaniline

A. 10.68 G (95% yield) was prepared by the method of Example 1B from 13 g of 3-bromo-4-fluoronitrobenzene. The product was an oil which was used without further purification. NMR (CDCl3, 250 MHz): 6.9 (m, 2H), 6.6 (m, 1H).

Ethyl 7-bromo-6-fluoro-4-hydroxyquinoline 3-carboxylate

B. 8.8 G (55% yield) was prepared by the method of Example 1C from 10 g 3-bromo-4-fluoroaniline and 11.36 g diethyl ethoxymethylene. A white solid of m.p. >280° C. was recovered. NMR (DMSO-d6/Trifluoroacetic acid-d, 250 MHz): 9.35 (s, 1H), 8.6 (d, 1H, J=6 Hz), 8.3 (d, 1H, J=11 Hz), 4.65 (q, 2H, J=6.5 Hz), 1.5 (t, 3H, J=6.5 Hz).

MS: Calcd. for C12H9FBrNO3: 312.9759. Found: 312.9766.

Ethyl 7-bromo-1-ethyl-6-fluoro-1,4-dihydroquinol-4-one 3-carboxylate

C. 5.2 G (55% yield) was prepared by the method of Example 1D from 8.6 g ethyl 7-bromo-6-fluoro-4-hydroxyquinoline 3-carboxylate. White solid of m.p. 149°–150° C.

NMR (CDCl3, 250 MHz): 8.45 (s, 1H), 8.15 (d, 1H, J=11 Hz), 7.7 (d, 1H, J=6 Hz), 4.4 (q, 2H, J=6.5 Hz), 4.2 (q, 2H, J=6.5 Hz), 1.55 (t, 3H, J=6.5 Hz), 1.4 (t, 3H, J=6.5 Hz).

MS: Calcd. for C14H13BrFNO3: 341.0062. Found: 341.0023.

Ethyl 1-ethyl-6-fluoro-7-(4-methoxyphenyl)-1,4-dihydroquinol-4-one 3-carboxylate D. 422 mg (64% yield) was prepared by the method of Example 13A from 500 mg 4-bromoanisole, 2.67 ml 2M t-butyl lithium, 500 mg anhydrous zinc chloride, 608 mg ethyl 7-bromo-1-ethyl-6-fluoro-1,4-dihydroquinol-4-one 3-carboxylate, and 300 mg tetrakis (triphenylphosphine)palladium. Yellow solid of m.p. 215°–218° C. NMR (CDCl3, 250 MHz): 8.45 (s, 1H), 8.2 (d, 1H, J=11 Hz), 7.55 (dd, 2H, J=9 Hz and 2 Hz), 7.45 (d, 1H, J=6 Hz), 7.0 (d, 2H, J=9 Hz), 4.4 (q, 2H, J=6.5 Hz), 4.3 (q, 2H, J=6.5 Hz), 3.9 (s, 3H), 1.6 (t, 3H, J=6.5 Hz), 1.45 (t, 3H, J=6.5 Hz).

1-Ethyl-6-fluoro-7-(4-methoxyphenyl)-1,4-dihydroquinol-4-one 3-carboxylic acid ($R_1=R_2=H$; Y=ethyl; $R_3$=4-methoxyphenyl)

E. 355 Mg (96% yield) was prepared by the method of Example 13B from 400 mg ethyl 1-ethyl-6-fluoro-7-(4-methoxyphenyl)-1,4-dihydroquinol-4-one 3-carboxylate. White solid of m.p. 279°–282° C.

NMR (DMSO-d6/Trifluoroacetic acid-d, 250 MHz): 9.4 (s, 1H), 8.4 (d, 1H, J=11 Hz), 8.3 (d, 1H, J=6 Hz), 7.75 (d, 2H, J=9 Hz), 7.2 (d, 2H, J=9 Hz), 5.0 (m, 2H), 4.0 (s, 3H), 1.8 (t, 3H, J=6.5 Hz).

MS: Calcd. for C19H16FNO4: 341.1064. Found: 341.1057.

Anal.: Calcd. for C19H16FNO4: C, 65.14; H, 4.86; N, 4.00%. Found: C, 65.19; H, 4.74; N, 3.91%.

EXAMPLE 27

1-Ethyl-6-fluoro-7-(4-hydroxyphenyl)-1,4-dihydroquinol-4-one 3-carboxylic acid

276 Mg (96% yield) was prepared by the method of Example 14 from 300 mg 1-ethyl-6-fluoro-7-(4-methoxyphenyl)-1,4-dihydroquinol-4-one 3-carboxylic acid. Yellow solid of m.p. >280° C. NMR (DMSO-d6/trifluoroacetic acid-d, 250 MHz): 9.0 (s, 1H), 8.0 (d, 1H, J=11Hz), 7.85 (d, 1H, J=6 Hz), 7.3 (d, 2H, J=9 Hz), 6.75 (d, 2H, J=9 Hz), 4.55 (m, 2H), 1.4 (t, 3H, J=6 Hz).

MS: Calcd. for C18H14FNO4: 327.0907. Found: 327.0930. Anal.: Calcd. for C18H14FNO4.1/8H2O: C, 65.60; H, 4.32; N, 4.25%. Found: C, 65.65; H, 4.43; N, 4.10%.

EXAMPLE 28

Ethyl 1-ethyl-6-fluoro-7-phenyl-1,4-dihydroquinol-4-one 3-carboxylate

173 Mg (51% yield) was prepared by the method of Example 1E from 0.72 ml (1.83M) phenyl lithium, 300 mg ethyl 7-bromo-6-fluoro-1,4-dihydroquinol-4-one 3-carboxylate, 192 mg zinc chloride and 104 mg tetrakis(triphenylphosphine) palladium. This sample was identical in every respect with that prepared in Example 4E. MS: Calcd. for C20H18FNO3: 339.1271. Found: 339.1257.

EXAMPLE 29

Ethyl 7-(4-t-butyl-dimethylsilyloxymethylphenyl)-1-ethyl-6-fluoro-1,4-dihydroquinol-4-one 3-carboxylate 301 Mg (31% yield) was prepared by the method of Example 2 from 1.51 g 4-bromobenzyl dimethyl-t-butylsilyl ether, 6.72 ml (2M) t-butyl lithium, 818 mg zinc chloride, 684 mg ethyl 7-bromo-1-ethyl-6-fluoro-1,4-dihydroquinol-4-one 3-carboxylate and 231 mg tetrakis(triphenylphosphine)palladium. The sample was identical in every way with that prepared in Example 15B. NMR (CDCl3, 250 MHz): 8.5 (s, 1H), 8.25 (d, 1H), 7.5 (q, 4H), 6.9 (d, 1H), 4.8 (s, 2H), 4.4 (q, 2H), 4.3 (q, 2H), 1.58 (t, 3H, J=7 Hz), 1.42 (t, 3H, J=7 Hz), 0.95 (s, 9H), 0.1 (s, 6H). MS: Calcd. for C22H34FNO4-Si:483.2241. Found: 483.2241.

EXAMPLE 30

Ethyl 7-(3-t-butyl-dimethylsilyloxymethylphenyl)-1-ethyl-6-fluoro-1,4-dihydroquinol-4-one 3-carboxylate 280 Mg (58% yield) was prepared by the method of Example 2 from 602 mg of 3-bromobenzyl dimethyl-t-butyl silyl ether, 1.64 ml (1.28M) t-butyl lithium, 341 mg zinc chloride, 342 mg ethyl 7-bromo-1-ethyl-6-fluoro-1,4-dihydroquinol-4-one 3-carboxylate and 115 mg tetrakis(triphenylphosphine)palladium. The sample was identical in every respect with that prepared in Example 16B. NMR (CDCl3, 90 MHz): 8.6 (s, 1H), 8.3 (d, 1H), 7.5 (m, 5H), 4.9 (s, 2H), 4.45 (q, 4H), 1.5 (5 line m, 6H), 0.95 (s, 9H), 0.1 (s, 6H).

MS: Calcd. for C27H34FNO4Si:483.2241. Found: 483.2195.

EXAMPLE 31

Ethyl 7-bromo-6,8-difluoro-1-(2-fluoroethyl)-1,4-dihydroquinol-4-one 3-carboxylate A. By the method of Example 1D, ethyl 7-bromo-6,8-difluoro-4-hydroxyquinoline-3-carboxylate (5.0 g, 15 mmol), anhydrous potassium carbonate (4.2 g, 30 mmol), 1-fluoro-2-bromo-ethane (25 g, 15 ml, 200 mmol) in dimethylformamide (50 ml) were reacted to give a white solid after recrystallization from 2-propanol (3.3 g, 58% yield), m.p. 185°–187° C.; IR (CHCl3, cm-1): 1732(s), 1695(s), 1461(s); NMR (CDCl3, 250 MHz): 8.39 (s, 1H), 8.14 (dd, 1H, J=10, 4 Hz), 4.95–4.85 (m, 2H), 4.78–4.55 (m, 2H), 4.40 (q, 2H, J=7 Hz), 1.40 (t, 3H, J=7 Hz).

Anal.: Calcd. for C14H11BrF3NO3: C, 44.49, H, 2.93, N, 3.71, Br, 21.14, F, 15.08: Found: C, 44.35, H, 2.98, N, 3.64, Br, 21.50, F, 14.65.

Ethyl 6,8-difluoro-7-(4-methoxyphenyl)-1-(2-fluoroethyl)-1,4-dihydroquinol-4-one 3-carboxylate B. By the method of Example 2, ethyl 7-bromo-6,8-difluoro-1-(2-fluoroethyl)-1,4-dihydroquinol-4-one 3-carboxylate (1.0 g, 2.7 mmol), 1-bromo-4-methoxybenzene (1.24 g, 0.83 ml, 6.6 mmol), a solution of t-butyl lithium in n-pentane (1.8M, 7.4 ml, 13.3 mmol), anhydrous zinc chloride (1.1 g, 8.0 mmol) and tetrakis(triphenylphosphine)palladium (306 mg) were reacted to give crude product as a yellow solid. Chromatography on silica gel with ethyl acetate afforded a solid (507 mg, 47% yield); m.p. 193°–195° C.; IR (KBr, cm-1): 1726 (s), 1612 (s) 1575 (m), 1541 (m), 1518 (m); NMR (CDCl3, 250 MHz): 8.42 (s, 1H), 8.16 (dd, 1H, J=10, 4 Hz), 7.43 (d, 2H, J=9 Hz), 7.05 (d, 2H, J=9 Hz), 4.95–4.65 (m, 4H), 4.42 (q, 2H, J=7 Hz), 3.91 (s, 3H), 1.42 (t, 3H, J=7 Hz).

Anal.: Calcd. for C21H18F3NO4.H20: C, 59.57, H, 4.76, N, 3.31. Found: C, 59.83, H, 4.33, N, 3.28.

6,8-Difluoro-7-(4-methoxyphenyl)-1-(2-fluoroethyl)-1,4-dihydroquinol-4-one 3-carboxylic acid C. By the method of Example 13B, ethyl 6,8-difluoro-7-(4-methoxyphenyl)-1-(2-fluoroethyl)-1,4-dihydroquinol-4-one 3-carboxylate (275 mg, 0.7 mmol) was hydrolyzed to give a white solid (191 mg, 75% yield); m.p. >270° C.; IR (KBr, cm-1): 1720 (s), 1621 (s), 1612 (s); NMR (1% DMSO-d6/CF3CO2D, 250 MHz): 8.90 (s, 1H), 7.90 (d, 1H, J=9 Hz), 7.22 (d, 2H, J=10 Hz), 6.80 (d, 2H, J=10 Hz), 4.95 (br. d, 2H, J=24 Hz), 4.65 (d, 2H, J=45 Hz), 3.57 (s, 3H).

Anal.: Calcd. for C19H14F3NO4.0.75 H20: C, 58.39, H, 3.99, N, 3.58. Found: C, 58.12, H, 3.75, N, 3.38.

EXAMPLE 32

6,8-Difluoro-7-(4-hydroxyphenyl)-1-(2-fluoroethyl)-1,4-dihydroquinol-4-one 3-carboxylic acid By the method of Example 14, 6,8-difluoro-7-(4-methoxyphenyl)-1-(2-fluoroethyl)-1,4-dihydroquinol-4-one 3-carboxylic acid (200 mg, 0.53 mmol) and a solution of boron tribromide in methylene chloride (1M, 5.3 ml, 5.3 mmol) were reacted to give crude product as a yellow solid. Trituration with boiling water afforded a white solid (131 mg, 66% yield); m.p. >280° C.; IR (KBr, cm-1): 1724 (s), 1610 (s), 1589 (s), 1567 (m); NMR (1% DMSO-d6/CF3CO2D, 250 MHz): 9.35 (s, 1H), 8.34 (d, 1H, J=10 Hz), 7.55 (d, 2H, J=9 Hz), 7.20 (d, 2H, J=9 Hz), 5.38 (d, 2H, J=24 Hz), 5.00 (d, 2H, J=45 Hz); MS: calcd. for C18H12F3NO4: 363.0719. Found: 363.0709

Anal.: Calcd. for C18H12F3NO4.H20: C, 56.70, H, 3.70, N, 3.67. Found: C, 56.99, H, 3.45, N, 3.67.

EXAMPLE 33

Ethyl 7-bromo-6,8-difluoro-1-methyl-1,4-dihydroquinol-4-one 3-carboxylate

A. By the method of Example 1D, ethyl 7-bromo-6,8-difluoro-4-hydroxyquinolinone-3-carboxylate (5.0 g, 15 mmol), anhydrous potassium carbonate (4.16 g, 30 mmol) and iodomethane (6.4 g, 2.8 ml, 45 mmol) in dimethylformamide (50 ml) were reacted to give a white solid, after recrystallization from 2-propanol (3.4 g, 66% yield); m.p. 174°–175° C.; IR (CHCl3, cm-1); 1732 (s), 1693 (s), 1642 (s), 1611 (s); NMR (CDCl3, 250 MHz): 8.40 (s, 1H), 8.00 (dd, 1H, J=10, 4 Hz), 4.35 (q, 2H, J=7 Hz), 4.08 (d, 3H, J=8 Hz), 1.58 (t, 3H, J=7 Hz).

Anal.: Calcd. for C13H10BrF2NO3: C, 45.13, H, 2.92, N, 4.05, Br, 23.10, F, 10.98. Found: C, 45.05, H, 2.70, N, 4.01, Br, 22.83, F, 10.52.

Ethyl 6,8-difluoro-7-(4-methoxyphenyl)-1-methyl-1,4-dihydroquinol-4-one 3-carboxylate B. By the method of Example 2, ethyl 7-bromo-6,8-difluoro-1-methyl-1,4-dihydroquinol-4-one-3-carboxylate (1.0 g, 2.9 mmol), 1-bromo-4-methoxybenzene (1.35 g, 0.91 ml, 7.3 mmol), a solution of t-butyl lithium in pentane (1.8M, 8.1 ml, 14.6 mmol) and anhydrous zinc chloride (1.31 g, 9.6 mmol) and tetrakis(triphenylphosphine) palladium (306 mg) were reacted to yield crude product as a yellow solid.. Column chromatography with ethyl acetate on silica gel afforded a solid (624 mg, 57% yield); m.p. 176°–178° C.; IR (KBr, cm-1): 1733 (m), 1684 (s), 1639 (s), 1617 (s), 1540 (m); NMR (CDCl3, 250 MHz): 8.38 (s, 1H), 8.08 (dd, 1H, J=10, 4 Hz), 7.42 (d, 2H, J=8 Hz), 7.05 (d, 2H, J=8 Hz), 4.41 (q, 2H, J=7 Hz), 4.12 (d, 3H, J=8 Hz), 3.90 (s, 3H), 1.42 (t, 3H, J=7 Hz); MS (m/e): 373 (parent), 201 (base).

Anal.: Calcd. for C20H13F2NO4.0.5H20: C., 62.83, H, 4.74, N, 3.66. Found: C, 63.22, H, 4.77, N, 3.42.

6,8-Difluoro-7-(4-methoxyphenyl)-1-methyl-1,4-dihydroquinol-4-one 3-carboxylic acid C. By the method of Example 13B, ethyl 6,8-difluoro-7-(4-methoxyphenyl)-1,4-dihydroquinol-4-one 3-carboxylate (446 mg, 1.2 mmol), was hydrolyzed to give a white solid (332 mg, 80% yield); m.p. >280° C.; IR (KBr, cm-1): 1718 (s), 1612 (s), 1567 (s), 1539 (s); NMR (CF3CO2D, 250 MHz): 9.30 (s, 1H), 8.25 (d, 1H, J=10 Hz), 7.65 (d, 2H, J=10 Hz), 7.22 (d, 2H, J=10 Hz), 4.70 (d, 3H, J=10 Hz), 3.96 (s, 3H); MS: Calcd. for C18H13F2NO4: 345.0812. Found: 345.0821.

Anal.: Calcd. for C18H13F2NO4: 62.61, H, 3.79, N, 4.06. Found: C, 62.43, H, 3.81, N, 3.95.

EXAMPLE 34

6,8-Difluoro-7-(4-hydroxyphenyl)-1-methyl-1,4-dihydroquinol-4-one 3-carboxylic acid By the method of Example 14, 6,8-difluoro-7-(4-methoxyphenyl)-1-methyl-1,4-dihydroquinol-4-one 3-carboxylic acid (202 mg, 0.6 mmol) and a solution of boron tribromide in methylene chloride (1M, 5.9 ml, 5.9 mmol) were reacted to give crude product as a yellow solid. Trituration with hot water afforded a white solid (126 mg, 65% yield); m.p. >270° C.; NMR (CF3CO2D, 250 MHz): 9.34 (s, 1H), 8.30 (d, 1H, J=10 Hz), 7.58 (d, 2H, J=10 Hz), 7.20 (d, 2H, J=10 Hz), 4.73 (d, 3H, J=10 Hz); MS: calcd. for C16H11F2NO2 (parent - CO2): 287.0758. Found: 287.0751.

Anal.: Calcd. for C17H11F2NO4.0.25H2O: C, 60.81, H, 3.45, N, 4.17. Found: C, 60.46, H, 3.33, N, 4.05.

EXAMPLE 35

Ethyl 7-bromo-6,8-difluoro-1-allyl-1,4-dihydroquinol-4-one 3-carboxylate

By the method of Example 1D, ethyl 7-bromo-6,8-difluoro-4-hydroxyquinoline 3-carboxylate (5.0 g, 15 mmol), anhydrous potassium carbonate (4.16 g, 30 mmol) and allyl bromide (5.4 g, 4 ml, 45 mmol) in dimethylformamide (50 ml) were reacted to give a white solid, after recrystallization from 2-propanol (4.2 g, 75% yield); m.p. 141°-143° C.; IR (CHCl3, cm-1): 1732 (s), 1694 (s), 1642 (s), 1610 (s), 1546 (m); NMR (CDCl3, 250 MHz): 8.40 (s, 1H), 8.12 (dd, 1H, J=10, 4 Hz); 6.15−6.00 (m, 1H), 5.35 (d, 1H, J=10 Hz), 5.18 (d, 1H, J=20 Hz), 5.00−4.86 (m, 2H), 4.40 (q, 2H, J=7 Hz), 1.40 (t, 3H, J=7 Hz).

Anal.: Calcd. for C15H12BrF2NO3: C, 48.43, H, 3.25, N, 3.77, Br, 21.48, F, 10.21. Found: C, 48.13, H, 3.28, N, 3.66, Br, 21.15, F, 10.29.

EXAMPLE 36

Ethyl 7-bromo-6,8-difluoro-1-benzyl-1,4-dihydroquinol-4-one 3-carboxylate

By the method of Example 1D, ethyl 7-bromo-6,8-difluoro-4-hydroxyquinoline 3-carboxylate (5.0 g, 15 mmol), anhydrous potassium carbonate (4.2 g, 30 mmol) and benzyl bromide (7.7 g, 5.4 ml, 45 mmol) in dimethylformamide (50 ml) were reacted to give a white solid after recrystallization from 2-propanol (4.4 g, 70% yield); m.p. 184°-186° C.; IR (CHCl3, cm-1): 1732 (s), 1695 (s), 1643 (s), 1610 (s), 1548 (m); NMR (CDCl3, 250 MHz): 8.50 (s, 1H), 8.10 (d, 1H, J=10 Hz) 7.45−7.25 (m, 3H), 7.17−7.05 (m, 2H), 5.55 (d, 2H, J=4 Hz), 4.40 (q, 2H, J=7 Hz), 1.40 (t, 3H, J=7 Hz).

Anal.: Calcd. for C19H14BrF2NO3: C, 54.05, H, 3.34, N, 3.32, Br, 18.90, F, 9.00. Found: C, 53.59, H, 3.30, N, 3.24, Br, 18.80, F, 9.10.

EXAMPLE 37

Ethyl 7-bromo-6,8-difluoro-1-propyl-1,4-dihydroquinol-4-one 3-carboxylate

A. By the method of Example 1D, ethyl 7-bromo-6,8-difluoro-4-hydroxyquinoline 3-carboxylate (5.0 g, 15 mmol), anhydrous potassium carbonate (4.16 g, 30 mmol) and 1-bromopropane (11 g, 8.2 ml, 90 mmol) in dimethylformamide (50 ml) were reacted to give a white solid, after recrystallization from 2-propanol (2.7 g, 48% yield); m.p. 139°-140° C.; IR (CHCl3, cm-1): 1731 (s), 1692 (s), 1641 (s), 1610 (s); NMR (CDCl3, 250 MHz); 8.40 (s, 1H), 8.15 (dd, 1H, J=10, 4 Hz), 4.42 (q 2H, J=7 Hz), 4.35−4.25 (m, 2H), 1.94 (sextet, 2H, J=7 Hz), 1.42 (t, 3H, j=7 Hz), 4.35-4.25 (m, 2H), 1.94 (sextet, 2H, J=7 Hz), 1.42 (t, 3H, J=7 Hz).

Anal.: Calcd. for C15H14BrF2NO3: C,48.17, H, 3.77, N, 3.75, Br, 21.37, F, 10.16. Found: C, 47.86, H, 3.73, N, 3.84, Br, 21.10, F, 10.35.

Ethyl 6,8-difluoro-7-(4-methoxyphenyl)-1-propyl-1,4-dihydroquinol-4-one 3-carboxylate B. By the method of Example 2, ethyl 7-bromo-6,8-difluoro-1-propyl-1,4-dihydroquinol-4-one 3-carboxylate (1.0 g, 2.7 mmol), 1-bromo-4-methoxybenzene (1.26 g, 0.84 ml, 6.75 mmol), anhydrous zinc chloride (1.1 g, 8.1 mmol), a solution of t-butyl lithium in pentane (1.8M, 7.5 ml, 13.5 mmol) and tetrakis(triphenylphosphine) palladium (320 mg ) were reacted to give crude product as a yellow solid. Chromatography with ethyl acetate on silica gel afforded a pale yellow solid (360 mg, 73% yield); m.p. 126°-128° C.; IR (KBR, cm-1): 1734 (s), 1612 (s), 1574 (m); NMR (CDCl3, 250 MHz): 8.45 (s, 1H), 8.15 (dd, 1H, J=10, 3 Hz), 7.42 (d, 2H, J=8 Hz), 7.05 (d, 2H, J=8 Hz), 4.44 (q, 2H, J=7 Hz), 3.92 (s, 3H), 3.35−3.25 (m, 2H), 2.00−1.85 (m, 2H), 1.45 (t, 3H, J=7 Hz), 1.00 (t, 3H, J=7 Hz).

Anal.: Calcd. for C22H21F2NO4. 0.25H2O: C, 65.10, H, 5.34, N, 3.45. Found: C, 65.22, H, 5.24, N, 3.38.

6,8-Difluoro-7-(4-methoxyphenyl)-1-propyl-1,4-dihydroquinol-4-one 3-carboxylic acid C. By the method of Example 13B, ethyl 6,8-difluoro-7-(4-methoxyphenyl)-1-propyl-1,4-dihydroquinol-4-one 3-carboxylate (245 mg, 0.6 mmol) was hydrolyzed to give a white solid (154 mg, 68% yield); m.p. 272°-274° C.; IR (KBr, cm-1): 1722 (s), 1612 (s); NMR (1% DMSO-d6/CF3CO2D, 250 MHz): 9.34 (s, 1H), 8.30 (d, 1H, J=8 Hz), 7.62 (d, 2H, J=8 Hz), 7.22 (d, 2H, J=8 Hz), 5.10−4.88 (m, 2H), 3.96 (s, 3H), 2.25−2.10 (m, 2H), 1.12 (t, 3H, J=7 Hz).MS: Calcd. for C20H17F2NO4: 373.1126. Found: 373.1146.

Anal.: Calcd. for C20H17F2NO4: C, 64.34, H, 4.59, N, 3.75. Found: C, 63.91, H, 4.49, N, 3.67.

EXAMPLE 38

6,8-Difluoro-7-(4-hydroxyphenyl)-1-propyl-1,4-dihydroquinol-4-one 3-carboxylic acid By the method of Example 14, 6,8-difluoro-7-(4-methoxyphenyl)-1-propyl-1,4-dihydroquinol-4-one 3-carboxylic acid (103 mg, 0.28 mmol) and a solution of boron tribromide in methylene chloride (1M, 2.8 ml, 2.8 mmol) were reacted to give crude product as a yellow solid. Trituration with boiling water and filtration afforded a white solid (98 mg, 98% yield); m.p. 262°-264° C.; IR (KBr, cm-1): 1721 (s), 1614 (m), 1561 (m); NMR (1% DMSO-d6/CF3CO2D, 250 MHz): 9.35 (s, 1H), 8.30 (d, 1H, J=8 Hz), 7.62 (d, 2H, J=8 Hz), 7.20 (d, 2H, J=8 Hz), 5.10−4.95 (m, 2H), 3.98 (s, 3H), 2.20−2.10 (m, 2H), 1.60−1.40 (m, 2H), 1.05 (t, 3H, J=7 Hz).

MS: Calcd. for C19H15F2NO4: 359.0980. Found: 359.0969.

EXAMPLE 39

Ethyl 7-bromo-6,8-difluoro-1-butyl-1,4-dihydroquinol-4-one 3-carboxylate

A. By the method of Example 1D, ethyl 7-bromo-6,8-difluoro-4-hydroxyquinoline 3-carboxylate (5.0 g, 15 mmol), anhydrous potassium carbonate (4.2 g, 30 mmol) and 1-bromobutane (18.5 g, 14.4 ml, 135 mmol) in dimethylformamide were reacted to give a white solid, after recrystallization from 2-propanol (3.1 g, 53% yield); m.p. 140°-141° C.; IR (CHCl3, cm-1): 1731 (s), 1692 (s), 1641 (s), 1610 (s), 1547 (m), 1480 (s); NMR (CDCl3, 250 MHz): 8.40 (s, 1H), 8.15 (dd, 1H, J=10, 4 Hz), 4.42 (q, 2H, J=7 Hz), 4.40−4.25 (m, 2H), 1.95−1.85 (m, 2H), 1.65−1.40 (m, 2H), 1.41 (t, 3H, J=7 Hz), 1.00 (t, 3H, J=7 Hz).

Anal.: Calcd. for C16H16BrF2NO3: C, 49.53, H, 4.16, N, 3.61, Br, 20.60, F, 9.79. Found: C, 49.65, H, 4.12, N, 3.56, Br, 20.59, F, 10.21.

Ethyl 6,8-difluoro-7-(4-methoxyphenyl)-1-butyl-1,4-dihydroquinol-4-one 3-carboxylate B. By the method of Example 2, ethyl 7-bromo-6,8-difluoro-1-butyl-1,4-dihydroquinol-4-one 3-carboxylate (1 g, 2.6 mmol), 1-bromo-4-methoxybenzene (1.22 g, 0.82 ml, 6.6 mmol), anhydrous zinc chloride (1.1 g, 8.1 mmol), a solution of t-butyl lithium in pentane (1.8M, 7.3 ml, 13.1 mmol) and tetrakis(triphenylphosphine)palladium (300 mg) were reacted to give crude product as a yellow solid, which was used without further purification.

6,8-Difluoro-7-(4-methoxyphenyl)-1-butyl-1,4-dihydroquinol-4-one 3-carboxylic acid C. By the method of Example 13B, ethyl 6,8-difluoro-7-(4-methoxyphenyl)-1-butyl-1,4-dihydroquinol-4-one 3-carboxylate was hydrolyzed to give a white solid (134 mg, 13% yield); m.p. 248°-249° C.; IR (KBr, cm-1): 1721 (s), 1614 (m), 1561 (m), 1538 (m); NMR (1% DMSO-d6/CF3CO2D, 250 MHz): 9.35 (s, 1H), 8.30 (d, 1H, J=8 Hz), 7.62 (d, 2H, J=8 Hz), 7.20 (d, 2H, J=8 Hz), 5.10−4.95 (m, 2H), 3.98 (s, 3H), 2.20−2.10 (m, 2H), 1.60−1.40 (m, 2H), 1.05 (t, 3H, J=7 Hz); MS: 387 (parent), 343 (base).

Anal.: Calcd. for C21H19F2NO4. 0.5 H2O: C, 63.63, H, 5.09, N, 3.53. Found: C, 63.73, H, 4.79, N, 3.46.

EXAMPLE 40

6,8-Difluoro-7-(4-hydroxyphenyl)-1-butyl-1,4-dihydroquinol-4-one 3-carboxylic acid By the method of Example 14, 6,8-difluoro-7-(4-methoxyphenyl)-1-butyl-1,4-dihydroquinol-4-one 3-carboxylic acid (91 mg, 0.24 mmol) and a solution of boron tribromide (1M, 2.4 ml, 2.4 mmol) were reacted to give crude product as a yellow solid. Trituration with boiling water, filtration and drying in vacuo afforded a white solid (40 mg, 45% yield); NMR (5% DMSO-d6/CF3CO2D, 250 MHz): 9.46 (s, 1H), 8.35 (d, 1H, J=10 Hz), 7.56 (d, 2H, J=10 Hz), 7.20 (d, 2H, J=10 Hz), 5.10−4.95 (m, 1H), 2.25−2.05 (m, 2H), 1.75−1.55 (m, 2H), 1.10 (t, 3H, J=7 Hz); MS: calcd. for C20H17F2NO4: 373.1126. Found: 373.1082.

Anal.: Calcd. for C20H17F2NO4. 0.75 H2O: C, 62.09, H, 4.82, N, 3.62. Found: C, 62.15, H, 4.82, N, 3.85.

EXAMPLE 41

Ethyl 6,8-difluoro-7-(4-chlorosulfonylphenyl)-1-ethyl-1,4-dihydroquinol-4-one 3-carboxylate A. By the method of Example 10A, ethyl 6,8-difluoro-7-phenyl-1-ethyl-1,4-dihydroquinol-4-one 3-carboxylate (0.55 g, 1.53 mmol) and chlorosulfonic acid (6 ml) were reacted in methylene chloride (10 ml) to give a yellow oil (0.7 g), which was used without further purification.

Ethyl 6,8-difluoro-7-(4-aminosulfonylphenyl)-1-ethyl-1,4-dihydroquinol-4-one 3-carboxylate B. Ethyl 6,8-difluoro-7-(4-chlorosulfonylphenyl)-1-ethyl-1,4-dihydroquinol-one 3-carboxylate (0.7 g) was dissolved in dry tetrahydrofuran (10 ml) and the resulting solution was cooled to −78° C. Ammonia (5 ml) was condensed into the reaction mixture with stirring. The reaction mixture was warmed to room temperature and stirred for 16 hours. Solvent was removed in vacuo and the crude product was triturated with water, then ether. Drying in vacuo afforded a pale yellow solid (0.6 g, 90% yield); m.p. >250° C.; NMR (3% DMSO-d6/CF3CO2D, 250 MHz): 9.38 (s, 1H), 8.40 (d, 1H, J=8 Hz), 8.20 (d, 2H, J=8 Hz), 7.95−7.85 (m, 2H), 7.72 (d, 2H, J=8 Hz), 5.20−5.05 (m, 2H), 4.72 (q, 4H, J=7 Hz), 1.80 (t, 3H, J=7 Hz), 1.55 (t, 3H, J=7 Hz) MS: Calcd. C20H18F2N2O5S: 436.0909. Found: 436.0912.

6,8-Difluoro-7-(4-aminosulfonylphenyl)-1-ethyl-1,4-dihydroquinol-4-one 3-carboxylic acid C. By the method of Example 10C, ethyl 6,8-difluoro-7-(4-aminosulfonylphenyl)-1-ethyl-1,4 -dihydroquinol-4-one-3-carboxylate (0.32 g, 0.73 mmol) and a 1N sodium hydroxide solution were reacted in ethanol (4 ml) to give a white solid (0.25 g, 84% yield); m.p. >250° C.; NMR (1% DMSO-d6/CF3CO2D, 250 MHz): 9.45 (s, 1H), 8.40 (d, 1H, J=8 Hz), 8.24 (d, 2H, J=8 Hz), 8.00−7.85 (m, 2H), 7.85 (m, 2H), 5.25−5.00 (m, 2H), 1.82 (t, 3H, J=7 Hz).

MS: Calcd. for C18H14F2N2O5S: 408.0580. Found: 408.0560.

Example 42

In addition, the following compounds were prepared:

TABLE I

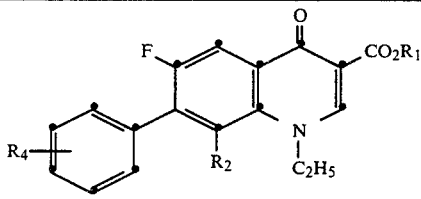

| R₁ | R₂ | R₄ | Melting point in °C. |
|---|---|---|---|
| $C_2H_5$ | F | 3-$SCH_3$ | 157–8 |
| $C_2H_5$ | F | 3-$CF_3$ | 133–4 |
| $C_2H_5$ | F | 3-F | 154–5 |
| $C_2H_5$ | F | 3-$CH_3$ | 172–3 |
| $C_2H_5$ | F | 3-F,4-$CH_3$ | 183–4 |
| $C_2H_5$ | F | 3-$CH_3$,4-$OCH_3$ | 199–200 |
| H | F | 3-$SCH_3$ | 250–2 |
| H | F | 3-$CF_3$ | 280–1 |
| H | F | 3-F | 297–8 |
| H | F | 3-$CH_3$ | 289–90 |
| $C_2H_5$ | F | 3-$S(O)CH_3$ | 165–6 |
| H | F | 3-$(S(O)CH_3$ | 277–8 |
| $C_2H_5$ | F | 3-$SO_2CH_3$ | 215–6 |
| H | F | 3-$SO_2CH_3$ | 242–3 |
| H | F | 3-$CH_2OH$,4-OH | 227–30 |
| H | F | 3-$CH_2N_3$ | 230–2 |
| H | F | 3-F,4-OH | 263–5 |
| H | F | 3-$CH_3$,4-OH | 263–5 |
| H | F | 3-$CH_3$,4-$OCH_3$ | 282–4 |
| H | F | 3-F,4-$OCH_3$ | 280–1 |
| $C_2H_5$ | F | 3,4-O—$CH_2$—O— | —(1) |
| H | F | 3,4-O—$CH_2$—O— | >260 |
| $C_2H_5$ | F | 4-C=NH<br>    \|<br>    $OC_2H_5$ | 134–6 |
| H | F | 4-$CO_2H$ | >260 |
| $C_2H_5$ | F | 2,4-di-$OCH_3$ | —(2) |
| H | F | 2,4-di-$OCH_3$ | >260 |
| $C_2H_5$ | F | 3,5-di-$OCH_3$ | —(3) |
| H | F | 3,5-di-$OCH_3$ | >260 |
| H | F | 2,4-di-OH | >260 |
| H | F | 3,5-di-OH | >260 |
| $C_2H_5$ | H | 3-F,4-$OCH_3$ | —(4) |
| H | H | 3-F,4-$OCH_3$ | >260 |
| H | H | 3-F,4-OH | >260 |
| $C_2H_5$ | H | 3-Cl,4-$OCH_3$ | 227–9 |
| H | H | 3-Cl,4-$OCH_3$ | >260 |
| H | H | 3-Cl,4-OH | >260 |
| $C_2H_5$ | H | 3,5-di-$CH_3$,4-$OCH_3$ | 228–30 |
| H | H | 3,5-di-$CH_3$,4-OH | 308–9 |

(1) NMR ($CDCl_3$, 60 MHz): 8.4 (s, 1H), 8.01 (dd, 1H, J = 2 Hz and 9 Hz), 6.95 (s, 3H), 6.05 (s, 2H), 4.4 (q, 4H), 1.45 (two overlapping triplets, 6H).
(2) NMR ($CDCl_3$, 60 MHz): 8.4 (s, 1H), 8.05 (d, 1H), 7.2 (m, 2H), 6.6 (s, 1H), 4.4 (m, 4H), 3.85 (s, 3H), 3.8 (s, 3H), 1.45 (m, 6H).
(3) NMR ($CDCl_3$, 60 MHz): 8.39 (s, 1H), 8.1 (dd, 1H), 6.58 (s, 3H), 4.4 (q, 4H), 3.9 (s, 6H), 1.5 (m, 6H).
(4) NMR ($CDCl_3$, 250 MHz): 8.55 (s, 1H), 8.27 (d, 1H), J = 13.5 Hz), 7.5 (m, 4H), 4.45 (q, 2H), 4.3 (q, 2H), 3.95 (s, 3H), 1.6 (t, 3H), 1.42 (t, 3H).

EXAMPLE 43

2,4-Difluoro-3-bromo-1-nitrobenzene

A. A solution of 1,3-difluoro-2-bromobenzene (23.5 g, 112 mmol) in concentrated sulfuric acid (48 ml) was stirred vigorously at ambient temperature. Concentrated nitric acid (70%, 8 ml) was added dropwise such that the internal temperature of the reaction mixture did not exceed 55° C. The reaction mixture was then stirred from 15 minutes and poured onto ice (300 ml). The aqueous mixture was extracted three times with methylene chloride. The combined organic layers were washed three times with a saturated sodium bicarbonate solution, dried over magnesium sulfate and filtered. Solvent was removed in vacuo to give a yellow solid. Recrystallization from isopropyl ether afforded a white solid (28.2 g, 97% yield): m.p. 50°–51.5° C. NMR ($CDCl_3$, 60 MHz): 8.4–7.9 (m, 1H), 7.4–7.0 (m, 1H).
Anal.: Calcd. for $C_6H_2BrF_2NO_2$: C, 30.28, H, 0.85, N, 5.89, Br, 33.57, F, 15.96. Found: C, 30.34, H, 0.98, N, 5.81, Br, 33.81, F, 16.04.

3-Bromo-4-fluoro-2-hydroxy-1-nitrobenzene

B. A solution of 3-bromo-2,4-difluoro-1-nitrobenzene (10.5 g, 44 mmol) in dimethyl sulfoxide (85 ml) was stirred at ambient temperature. A solution of potassium hydroxide (14.1 g, 251 mmol) in water (21 ml) was added dropwise over 15 minutes. The black reaction mixture was stirred at ambient temperature for 16 hours. The reaction mixture was then poured onto water (200 ml) and three ether extractions (100 ml) were performed. The aqueous layer was acidified with concentrated hydrochloric acid and extracted three times with ether (100 ml). The combined organic layers were dried over magnesium sulfate and filtered. Solvent was removed in vacuo to give a yellow solid (9.7 g, 93% yield). Recrystallization from isopropyl ether afforded an analytical sample: m.p. 65°–66° C. NMR ($CDCl_3$, 60 MHz): 8.1 (dd, 1H, J=10, 5 Hz), 6.8 (dd, 1H, J=10, 8 Hz)
Anal.: Calcd. for $C_6H_3BrFNO_3$: C, 30.54, H, 1.30, N, 5.94, Br, 33.86, F, 8.05. Found: C, 30.52, H, 1.27, N, 5.70, Br, 33.56, F, 7.96.

1-(2-Bromo-3-fluoro-6-nitrophenoxy)-propan-2-one

C. Chloroacetone (3.8 g, 3.3 ml, 41 mmol) was added dropwise to a solution of 3-bromo-4-fluoro-2-hydroxy-1-nitrobenzene (4.3 g, 18.2 mmol) in acetone (54 ml) with stirring at ambient temperature. Potassium carbonate (5.8 g, 42 mmol) and potassium iodide (6.0 g, 36.4 mmol), were added and the reaction mixture was heated to reflux temperature for 2 hours. The reaction mixture was then cooled to room temperature, poured onto water (100 ml), and extracted three times with ethyl acetate (150 ml). The combined organic layers were dried over magnesium sulfate, treated with decolorizing charcoal and filtered through diatomaceous earth. Solvent was removed in vacuo to afford a dark brown oil. Chromatography on silica gel with ethyl acetatehexanes (1:1) afforded, after removal of solvent in vacuo, a dark brown liquid (Rf=0.67, 3.5 g, 66% yield): NMR($CDCl_3$, 60 MHz): 8.1 (dd, 1H, J=10, 6 Hz), 7.4 (dd, 1H, J=10, 8 Hz), 4.6 (s, 2H), 2.3 (s, 3H).

8-Bromo-7-fluoro-3-methyl-2,3-dihydro-1,4-benzoxazine

D. Raney nickel (0.5 g) in absolute ethanol (10 ml) was added to a solution of 1-(2-bromo-4-fluoro-6-nitrophenoxy)-propan-2-one (2.1 g, 7.2 mmol) in absolute ethanol (200 ml). The reaction mixture was then shaken in a Parr apparatus under a hydrogen atmosphere (15 psi) for 1 hour. The reaction mixture was then filtered through diatomaceous earth. Solvent was removed in vacuo to afford a dark brown oil (1.5 g, 85% yield): NMR ($CDCl_3$, 60 MHz): 6.7–6.5 (m, 2H), 4.5–3.7 (m, 3H), 1.3 (d, 3H, J=7 Hz).
Anal.: Calcd. for $C_9H_9BrFNO$: C, 43.93, H, 3.69, N, 5.69; Found C, 43.96, H, 3.89, N, 5.14.

Ethyl 10-bromo-9-fluoro-3-methyl-7-oxo-2,3-dihydro-(7H)-pyrido-(1,2,3-de)-1,4-benzoxazine-6-carboxylate E. 8-Bromo-7-fluoro-3-methyl-2,3-dihydro-1,4-benzoxazine (3 g, 12.2 mmol) and diethyl ethoxymethylenemalonate (2.8 g, 2.6 ml, 12.9 mmol) were heated at 140° C. under a nitrogen atmosphere for 1 hour, then under reduced pressure (5 psi) for 0.5 hour. The crude product, diethyl 2-(8-bromo-7-fluoro-3-methyl-2,3-dihydro-1,4-benzoxazinyl)methylenepropane-1,3-dioate, was used without further purification.

The above product was stirred with polyphosphoric ester (10 g) at 140° C. under a nitrogen atmosphere for 1 hour. The reaction mixture was then poured onto water (200 ml). The aqueous mix was made basic (pH=10 by test paper) with a saturated sodium hydroxide solution and extracted three times with chloroform (200 ml). The combined organic layers were dried over magnesium sulfate, treated with decolorizing charcoal and filtered through diatomaceous earth. Solvent was removed in vacuo to give a solid. The solid was suspended in a saturated sodium bicarbonate solution (100 ml) and stirred for 30 minutes. The suspension was extracted three times with chloroform and the combined organic layers were dried over magnesium sulfate. Solvent was removed in vacuo to give a solid. Trituration with ether, filtration and drying in vacuo afforded a white solid (2.4 g, 53% yield): m.p. >250° C. NMR (CDCl3, 250 MHz): 8.35 (s, 1H), 7.75 (d, 1H, J=8 Hz), 4.60−4.30 (m, 3H), 4.48 (q, 2H, J=7 Hz), 1.60 (d, 3H, J=7 Hz), 1.40 (t, 3H, J=7 Hz).

Anal.: Calcd. for C15H13BrFNO4: C, 48.67, H, 3.54, N, 3.78, Br, 21.59, F, 5.13. Found: C, 48.44, H, 3.56, N, 3.66, Br, 21.60, F, 5.25.

10-Bromo-9-fluoro-3-methyl-7-oxo-2,3-dihydro-(7H)-pyrido-(1,2,3-de)-1,4-benzoxazine-6-carboxylic acid F. A mixture of ethyl 10-bromo-9-fluoro-3-methyl-7-oxo-2,3-dihydro-(7H)-pyrido-(1,2,3-de)-1,4-benzoxazine-6-carboxylate (0.2 g, 0.54 mmol) and a 3N hydrochloric acid solution (15 ml) were heated at 100° C. with stirring for 17 hours. The reaction mixture was diluted twofold with water and filtered. The white solid, which was collected, was washed with water, triturated with acetone, and filtered. Drying in vacuo afforded a white powder (142 mg, 77% yield): m.p. >250° C. NMR (5% DMSO-d6/CF3CO2D, 250 MHz): 9.12 (s, 1H), 7.80 (d, 1H, J=8 Hz), 5.10−5.00 (m, 1 H), 4.80−4.70 (m, 1H), 4.60−4.50 (m, 1H), 1.52 (d,3H, J=7 Hz).

Anal. Calcd. for C13H9BrFNO4: C, 45.64, H, 2.65, N, 4.09; Found: C, 45.70, H, 2.64, N, 3.90.

Ethyl 9-fluoro-10-phenyl-3-methyl-7-oxo-2,3-dihydro-(7H)-pyrido-(1,2,3-de)-1,4-benzoxazine-6-carboxylate G. A solution of phenyl lithium (2.7M) in etherbenzene [(3:7), 1.5 ml, 4 mmol] was added to dry tetrahydrofuran (10 ml) and the resulting solution was cooled to −78° C. with stirring under a nitrogen atmosphere. A solution of freshly fused zinc chloride (0.54 g, 4 mmol) in dry tetrahydrofuran (10 ml) was added dropwise over 5 minutes. The clear, colorless solution was warmed to −30° C. over 20 minutes. Ethyl 9-fluoro-10-bromo-3-methyl-7-oxo-2,3-dihydro-(7H)-pyrido-(1,2,3-de)-1,4-benzoxazine-6-carboxylate (1.0 g, 2.7 mmol) was added in one portion; then dichlorobis(triphenylphosphine) nickel (0.13 g, 0.2 mmol) was added in one portion. The reaction mixture was gradually warmed to ambient temperature and stirred for 24 hours. The dark brown mixture was poured onto a 1N hydrochloric acid solution (100 ml) and the aqueous mix was stirred for 15 minutes. Three extractions with chloroform (50 ml), drying the combined organic layers over magnesium sulfate, treatment with decolorizing charcoal and filtration through diatomaceous earth gave a yellow solution. Removal of solvent in vacuo afforded a bright yellow solid. Trituration with ether, filtration and drying in vacuo gave a pale yellow solid (0.67 g, 46% yield): m.p. 270°–272° C. NMR (CDCl3, 250 MHz): 8.42 (s, 1H), 7.85 (d, 1H, J=10 Hz), 7.55−7.40 (m, 5H), 4.42 (q, 2H, J=7 Hz), 4.50−4.35 (m, 3H), 1.62 (d, 3H, J=8 Hz), 1.45 (t, 3H, J=7 Hz).

MS: Calcd for C21H18FNO4: 367.1223. Found: 367.1179.

9-Fluoro-10-phenyl-3-methyl-7-oxo-(7H)-2,3-dihydro-(1,2,3-de)-1,4-benzoxazine 6-carboxylic acid ($R_1$=H, $R_3$=phenyl and $R_2$ and Y are taken together forming -O-CH2-CH2-)

H. Ethyl 9-fluoro-10-phenyl-3-methyl-7-oxo-(7H)-2,3-dihydro-(1,2,3-de)-1,4-benzoxazine-6-carboxylate (420 mg, 1,1 mmol) was suspended in a 1N hydrochloric acid solution (10 ml) and ethanol (10 ml). The suspension was heated at 90° C. with stirring. The suspension was cooled to ambient temperature and filtered. The collected solid was washed with water, then with methanol. Drying in vacuo gave a pale yellow solid (0.3 g, 80% yield): m.p. >250° C. NMR (1% DMSO-d6/CF3CO2D, 250 MHz): 8.92 (s, 1H), 7.64 (d, 1H, J=10 Hz), 7.30−7.10 (m, 5H), 4.85−4.70 (m, 1H), 4.35−4.15 (m, 2 H), 1.42 (d, 3H, J=8 Hz).

MS: Calcd for C19H14FNO4: 339.0907 Found: 339.0911.

EXAMPLE 44

Ethyl 9-fluoro-10-(4-chlorosulfonylphenyl)-3-methyl-7-oxo-2,3-dihydro-(7H)-pyrido-(1,2,3-de)-1,4-benzoxazine-6-carboxylate A. A suspension of ethyl 9-fluoro-10-phenyl-3-methyl-7-oxo-2,3-dihydro-(7H)-pyrido-(1,2,3-de)-1,4-benzoxazine-6-carboxylate (0.4 g, 1.2 mmol) in dichloromethane (15 ml) was cooled to 0° C. with stirring. Chlorosulfonic acid (5 ml) was added dropwise over 5 minutes. The dark solution was stirred at 0° C. for 15 minutes, then it was warmed gradually to room temperature over 1.5 hour. The reaction mixture was poured onto ice water with stirring. Three extractions with chloroform, drying the combined organic layers over magnesium sulfate, filtration and removal of solvent in vacuo gave a yellow oil (0.5 g) which was used without further purification.

Ethyl 9-fluoro-10-(4-aminosulfonylphenyl)-3-methyl-7-oxo-2,3-dihydro-(7H)-pyrido(1,2,3-de)-1,4-benzoxazine-6-carboxylate B. Ethyl 9-fluoro-10-(4-chlorosulfonylphenyl)-3-methyl-7-oxo-2,3-dihydro-(7H)-pyrido-(1,2,3-de)-1,4-benzoxazine-6-carboxylate (0.5 g) was dissolved in dry tetrahydrofuran (80 ml) and the resulting solution was cooled to −78° C. with stirring. Ammonia (5 ml) was condensed into the reaction mixture and the yellow suspension was warmed gradually to ambient temperature over 16 hours. Solvent was removed in vacuo and the residue was triturated with water and filtered. Drying in vacuo afforded a solid (0.3 g, 56% yield): m.p. >250° C. NMR (DMSO-d6, 250 MHz): 8.74 (s, 1H), 7.96 (d, 2H, J=10 Hz), 7.74 (d, 2 H, J= 10 Hz), 7.60 (d, 1H, J=10 Hz), 7.50 (s, 2H), 4.90−4.75 (m, 1H), 4.55−4.45 (m, 2H), 4.25 (q, 2H, J=7 Hz), 1.45 (d, 3H, J=7 Hz), 1.30 (t, 3H, J=7 Hz).

Anal.: Calcd. for C21H19FN2O6S: C, 56.50, H, 4.29, N, 6.27. Found: C, 56.13, H, 4.52, N, 6.18.

9-Fluoro-10-(4-aminosulfonylphenyl)-3-methyl-7-oxo-2,3-dihydro-(7H)-pyrido-(1,2,3-de)-1,4-benzoxazine-6-carboxylic acid C. A mixture of ethyl 9-fluoro-10-(4-aminosulfonylphenyl)-3-methyl-7-oxo-2,3-dihydro-(7H)-pyrido-(1,2,3-de)-1,4-benzoxazine-6-carboxylate (250 mg, 0.6 mmol), a 1N sodium hydroxide solution (7 ml) and ethanol (7 ml) was heated at 90° C. with stirring for 30 minutes. The reaction mixture was cooled to ambient temperature and was concentrated in vacuo. The milky suspension was neutralized with a 1N hydrochloric acid solution. The precipitate was filtered and washed with water. Drying in vacuo afforded a white powder (160 mg, 68% yield): m.p. >250° C. NMR (1% DMSO-d6/CF3CO2D, 250 MHz): 8.95 (s, 1H), 7.74 (d, 2H, J=10 Hz), 7.65 (d, 1H, J=10 Hz), 7.37 (d, 2H, J=10 Hz), 4.85−4.70 (m, 1H), 4.30−4.15 (m, 2H), 1.40 (d, 3H, J=7 Hz).

Anal.: Calcd. for C19H15FN2O6.2 H2O: C, 50.21, H, 4.21, N, 6.16. Found: C, 50.50, H, 3.55, N, 6.25.

The following Table sets out the in vitro antibacterial activity of compounds of the invention and compares then with Compound A according to U.S. Pat. No. 3,472,859. The advantageous bacterial activity over Compound A is clearly shown.

TABLE II

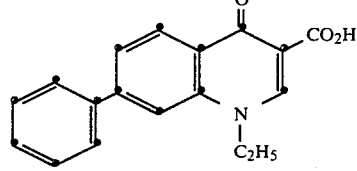

Compound A

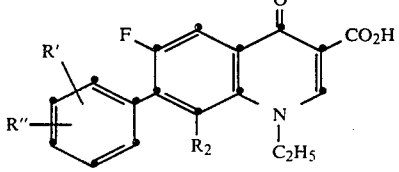

(I')

| $R_2$ | R' | R" | Facultatively anaerobic | | | Obligately Anaerobic | |
|---|---|---|---|---|---|---|---|
| | | | E. coli | S. choler. | St. Aureus | B. fragilis | F. necro. |
| Compound A | | | 6.25 | 6.25 | 1.56 | 25 | 25 |
| H | H | H | 0.2 | 0.2 | 0.05 | 25 | 25 |
| H | 4-NH2 | H | 0.1 | 0.1 | 0.05 | 1.56 | 1.56 |
| H | 4-NO2 | H | 0.78 | 0.78 | 0.1 | 3.12 | 1.56 |
| H | 4-NHCHO | H | 0.39 | 0.39 | 0.1 | 0.78 | 0.78 |
| H | 4-NHAc | H | 0.78 | 0.78 | 0.1 | 3.12 | 3.12 |
| H | 4-N=CHNMe2 | H | 0.78 | 0.78 | 0.2 | 3.12 | 3.12 |
| H | 4-SO2NH2 | H | 0.78 | 0.78 | 0.39 | 0.78 | 0.78 |
| H | 4-CHO | H | 0.78 | 0.78 | | | |
| H | 4-CH2OH | H | 0.39 | 0.39 | 0.05 | 0.2 | 0.39 |
| H | 3-CH2OH | H | 0.78 | 0.78 | 0.1 | 3.12 | 3.12 |
| F | H | H | 12.5 | 12.5 | 0.39 | | |
| F | 4-OH | H | 0.39 | 0.39 | 0.05 | 0.78 | 0.39 |

TABLE II-continued

Compound A (I')

| $R_2$ | R' | R" | Facultatively anaerobic | | | Obligately Anaerobic | |
|---|---|---|---|---|---|---|---|
| | | | E. coli | S. choler. | St. Aureus | B. fragilis | F. necro. |
| F | 4-OMe | H | 1.56 | 0.39 | 0.05 | | |
| F | 3-OH | H | 0.39 | 0.39 | 0.05 | | |
| F | 4-OH | 3-Cl | 0.39 | 0.39 | 0.05 | 1.56 | 1.56 |
| F | 4-CH2OH | H | 0.39 | 0.39 | 0.05 | | |
| F | 3-CH2OH | H | 0.78 | 0.78 | 0.1 | | |
| F | 4-CH2NH2 | H | 0.1 | 0.1 | 0.2 | 0.39 | 0.2 |
| F | 3-CH2NH2 | H | 0.2 | 0.2 | 0.2 | | |
| F | 4-SOMe | H | 1.56 | 1.56 | 0.2 | 0.78 | 1.56 |
| F | 2-OH | H | | | | | |

We claim:
1. A compound selected from those of the formula:

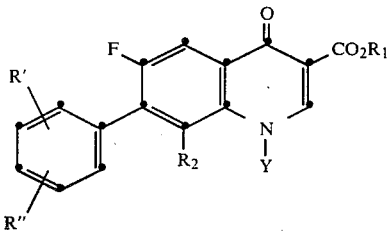

wherein $R^1$ is hydrogen, alkyl of 1 to 6 carbon atoms, benzyl or a pharmaceutically acceptable cation;

$R^2$ is hydrogen or fluoro;

Y is alkyl, haloalkyl or polyhaloalkyl of 1 to 3 carbon atoms, hydroxyethyl, cyclopropyl, vinyl, allkyl, phenyl, 4-hydroxyphenyl or 4-fluorophenyl;

R' is hydrogen, alkylsulfinyl or alkylsulfonyl of 1 to 4 carbon atoms, hydroxy, hydroxyalkyl of 1 to 3 carbon atoms, amino, aminoalkyl of 1 to 3 carbon atoms, formamido, alkanoylamino of 2 or 3 carbon atoms, aminosulfonyl, nitro, formyl, N-(N',N'-dimethylformamidino); and R" is hydrogen, 3-hydroxy or 3-chloro; provided that R' and R" are not both hydrogen.

2. A compound as claimed in claim 1 wherein $R_1$ is hydrogen or a pharmaceutically acceptable cation.

3. A compound as claimed in claim 2 wherein Y is ethyl.

4. A compound as claimed in claim 3 wherein $R_2$ is fluorine.

5. A compound as claimed in claim 4 wherein said compound is selected from the group consisting of 6,8-difluoro-7-(4-hydroxyphenyl)-1-ethyl-1,4-dihydroquinol-4-one 3-carboxylic acid
6,8-difluoro-7-(3-chloro-4-hydroxyphenyl)-1-ethyl-1,4-dihydroquinol-4-one 3-carboxylic acid
6,8-difluoro-7-(3-hydroxyphenyl)-1-ethyl-1,4-dihydroquinol-4-one 3-carboxylic acid
6,8-difluoro-7-(4-aminomethylphenyl)-1-ethyl-1,4-dihydroquinol-4-one 3-carboxylic acid
6,8-difluoro-7-(3-aminomethylphenyl)-1-ethyl-1,4-dihydroquinol-4-one 3-carboxylic acid
6,8-difluoro-7-(4-hydroxymethylphenyl)-1-ethyl-1,4-dihydroquinol-4-one 3-carboxylic acid
6,8-difluoro-7-(3-hydroxymethylphenyl)-1-ethyl-1,4-dihydroquinol-4-one 3-carboxylic acid
6,8-difluoro-7-(4-methylsulfinylphenyl)-1-ethyl-1,4-dihydroquinol-4-one 3-carboxylic acid
6,8-difluoro-7-(3-methylsulfonylphenyl)-1-ethyl-1,4-dihydroquinol-4-one 3-carboxylic acid
6,8-difluoro-7-(4-methoxyphenyl)-1-ethyl-1,4-dihydroquinol-4-one 3-carboxylic acid and
6,8-difluoro-7-(3-hydroxymethyl-4-hydroxy)-1-ethyl-1,4-dihydroquinol-4-one 3-carboxylic acid.

6. A compound as claimed in claim 3 wherein $R_2$ is hydrogen.

7. A compound as claimed in claim 6 wherein said compound is selected from the group consisting of
6-fluoro-7-(4-aminophenyl)-1-ethyl-1,4-dihydroquinol-4-one 3-carboxylic acid
6-fluoro-7-(4-nitrophenyl)-1-ethyl-1,4-dihydroquinol-4-one 3-carboxylic acid
6-fluoro-7-(4-formamidophenyl)-1-ethyl-1,4-dihydroquinol-4-one 3-carboxylic acid
6-fluoro-7-(4-acetamidophenyl)-1-ethyl-1,4-dihydroquinol-4-one 3-carboxylic acid
6-fluoro-7-(4-N-(N',N'-dimethylformamidino)-phenyl)-1-ethyl-1,4-dihydroquinol-4-one 3-carboxylic acid
6-fluoro-7-(4-formylphenyl)-1-ethyl-1,4-dihydroquinol-4-one 3-carboxylic acid
6-fluoro-7-(4-hydroxymethylphenyl)-1-ethyl-1,4-dihydroquinol-4-one 3-carboxylic acid
6-fluoro-7-(3-hydroxymethylphenyl)-1-ethyl-1,4-dihydroquinol-4-one 3-carboxylic acid and
6-fluoro-7-(4-aminosulfonylphenyl)-1-ethyl-1,4-dihydroquinol-4-one 3-carboxylic acid.

8. A compound as claimed in claim 1 wherein said compound is 9-fluoro-10-(4-aminosulfonylphenyl)-3-methyl-7oxo-2,3-dihydro-(7H)-pyrido-(1,2,3-de)-1,4-benzoxazine-6-carboxylic acid.

9. An antibacterial composition comprising a compound as claimed in claim 1 in an amount sufficient for treament of a bacterial disease and a pharmaceutically acceptable carrier.

10. A composition as claimed in claim 9 wherein said compound is selected from the group consisting of
6,8-difluoro-7-(4-hydroxyphenyl)-1-ethyl-1,4-dihydroquinol-4-one 3-carboxylic acid
6,8-difluoro-7-(3-chloro-4-hydroxyphenyl)-1-ethyl-1,4-dihydroquinol-4-one 3-carboxylic acid
6,8-difluoro-7-(3-hydroxyphenyl)-1-ethyl-1,4-dihydroquinol-4-one 3-carboxylic acid
6,8-difluoro-7-(4-aminomethylphenyl)-1-ethyl-1,4-dihydroquinol-4-one 3-carboxylic acid
6,8-difluoro-7-(3-aminomethylphenyl)-1-ethyl-1,4-dihydroquinol-4-one 3-carboxylic acid
6,8-difluoro-7-(4-hydroxymethylphenyl)-1-ethyl-1,4-dihydroquinol-4-one 3-carboxylic acid
6,8-difluoro-7-(3-hydroxymethylphenyl)-1-ethyl-1,4-dihydroquinol-4-one 3-carboxylic acid
6,8-difluoro-7-(4-methylsulfinylphenyl)-1-ethyl-1,4-dihydroquinol-4-one 3-carboxylic acid
6,8-difluoro-7-(3-methylsulfonylphenyl)-1-ethyl-1,4-dihydroquinol-4-one 3-carboxylic acid
6,8-difluoro-7-(4-methoxyphenyl)-1-ethyl-1,4-dihydroquinol-4-one 3-carboxylic acid and
6,8-difluoro-7-(3-hydroxymethyl-4-hydroxy)-1-ethyl-1,4-dihydroquinol-4-one 3-carboxylic acid.

11. A composition as claimed in claim 9 wherein said compound is selected from the group consisting of
6-fluoro-7-(4-aminophenyl)-1-ethyl-1,4-dihydroquinol-4-one 3-carboxylic acid
6-fluoro-7-(4-nitrophenyl)-1-ethyl-1,4-dihydroquinol-4-one 3-carboxylic acid
6-fluoro-7-(4-formamidophenyl)-1-ethyl-1,4-dihydroquinol-4-one 3-carboxylic acid
6-fluoro-7-(4-acetamidophenyl)-1-ethyl-1,4-dihydroquinol-4-one 3-carboxylic acid
6-fluoro-7-(4-N-(N',N'-dimethylformamidino)-phenyl)-1-ethyl-1,4-dihydroquinol-4-one 3-carboxylic acid
6-fluoro-7-(4-formylphenyl)-1-ethyl-1,4-dihydroquinol-4-one 3-carboxylic acid
6-fluoro-7-(4-hydroxymethylphenyl)-1-ethyl-1,4-dihydroquinol-4-one 3-carboxylic acid
6-fluoro-7-(3-hydroxymethylphenyl)-1-ethyl-1,4-dihydroquinol-4-one 3-carboxylic acid and
6-fluoro-7-(4-aminosulfonylphenyl)-1-ethyl-1,4-dihydroquinol-4-one 3-carboxylic acid.

12. A composition as claimed in claim 9 wherein said compound is 9-fluoro-10-(4-aminosulfonylphenyl)-3-methyl-7-oxo-2,3-dihydro-(7H)-pyrido-(1,2,3-de)-1,4-benzoxazine-6-carboxylic acid.

13. A method for treating a host infected by a bacterial disease which comprises administering to said host an antibacterially effective amount of a compound as claimed in claim 1.

14. A compound according to claim 1 wherein said compound is 6-fluoro-7-(4-hydroxyphenyl)-1-(4-fluorophenyl)-1,4-dihydroquinol-4-one 3-carboxylic acid.

15. A composition according to claim 9 wherein said compound is 6-fluoro-7-(4-hydroxyphenyl)-1-(4-fluorophenyl)-1,4-dihydroquinol-4-one 3-carboxylic acid.

16. A composition for the treatment of St. aureus which comprises 6-fluoro-7-phenyl-1-Y-1,4-dihydroquinol-4-one 3-carboxylic acid or 6,8-difluoro-7-phenyl-1-Y-1,4-dihydroquinol-4-one 3-carboxylic acid wherein Y is alkyl, haloalkyl or polyhaloalkyl of 1 to 3 carbon atoms, hydroxyethyl, cyclopropyl, vinyl, allyl, phenyl, 4-hyroxyphenyl or 4-fluorphenyl, in an amount sufficient for treatment of St. aureus, and a pharmaceutically acceptable carrier.

17. A method for treating a host infected by St. aureus which comprises administering to said host 6-fluoro-7-phenyl-1-Y-1,4-dihydroquinol-4-one 3-carboxylic acid or 6,8-difluoro-7-phenyl-1-Y-1,4-dihydroquinol-4-one 3-carboxylic acid wherein Y is alkyl, haloalkyl or polyhaloalkyl of 1 to 3 carbon atoms, hydroxyethyl, cyclopropyl, vinyl, allyl, phenyl, 4-hydroxyphenyl or 4-fluorophenyl in an amount sufficient for treatment of St. aureus.

* * * * *